(12) United States Patent
Fukasaka et al.

(10) Patent No.: US 10,092,642 B2
(45) Date of Patent: *Oct. 9, 2018

(54) MUCOSAL VACCINE COMPOSITION

(71) Applicant: NITTO DENKO CORPORATION, Osaka (JP)

(72) Inventors: Masahiro Fukasaka, Osaka (JP); Mitsuhiko Hori, Osaka (JP); Katsuyuki Okubo, Osaka (JP); Daisuke Asari, Osaka (JP); Arimichi Okazaki, Osaka (JP); Eiji Kiyotoh, Osaka (JP); Kyohei Matsushita, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/917,084

(22) PCT Filed: Oct. 2, 2014

(86) PCT No.: PCT/JP2014/076349
§ 371 (c)(1),
(2) Date: Mar. 7, 2016

(87) PCT Pub. No.: WO2015/050180
PCT Pub. Date: Apr. 9, 2015

(65) Prior Publication Data
US 2016/0193327 A1    Jul. 7, 2016

(30) Foreign Application Priority Data

Oct. 3, 2013 (JP) ................ 2013-208663

(51) Int. Cl.
*A61K 39/00* (2006.01)
*A61K 39/385* (2006.01)
(Continued)

(52) U.S. Cl.
CPC ........... *A61K 39/385* (2013.01); *A61K 9/006* (2013.01); *A61K 39/04* (2013.01); *A61K 39/08* (2013.01); *A61K 39/092* (2013.01); *A61K 39/12* (2013.01); *A61K 39/13* (2013.01); *A61K 39/145* (2013.01); *A61K 39/15* (2013.01); *A61K 39/155* (2013.01); *A61K 39/165* (2013.01); *A61K 39/20* (2013.01);
(Continued)

(58) Field of Classification Search
None
See application file for complete search history.

(56) References Cited

U.S. PATENT DOCUMENTS

| 6,010,719 A * | 1/2000 | Remon ............... A61K 9/2018 424/435 |
| 9,498,527 B2 | 11/2016 | Fukasaka et al. |
| 2005/0152919 A1* | 7/2005 | Ward ............... A61K 39/165 424/212.1 |
| 2008/0279926 A1 | 11/2008 | Vandepapeliere |
| 2010/0312045 A1 | 12/2010 | Ramlov et al. |
| 2013/0089570 A1 | 4/2013 | Ouaked et al. |
| 2013/0266612 A1* | 10/2013 | Fukasaka ............... A61K 39/39 424/210.1 |
| 2014/0193460 A1 | 7/2014 | Spector et al. |
| 2014/0220058 A1 | 8/2014 | Maeda et al. |
| 2014/0220059 A1 | 8/2014 | Asari et al. |

(Continued)

FOREIGN PATENT DOCUMENTS

| JP | H08-245702 A | 9/1996 |
| JP | 4043533 B2 | 2/2008 |

(Continued)

OTHER PUBLICATIONS

Mizuno et al. (Google machine translation of JP Patent 08-245702, 1996; IDS filed Oct. 2, 2014).*

(Continued)

*Primary Examiner* — Brian Gangle
(74) *Attorney, Agent, or Firm* — Greenblum & Bernstein, P.L.C.

(57) ABSTRACT

The present invention aims at providing a mucosal vaccine composition that can be administered to an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane, that is useful as a prophylactic or therapeutic agent for infectious diseases or cancers, and is capable of safely and effectively inducing the systemic immune response and mucosal immune response. The present invention provides a mucosal vaccine composition to be administered to at least one mucous membrane selected from the group consisting of a human or animal intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, and rectal mucous membrane, containing: at least one antigen; and as an adjuvant, a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas*, and *Enterobacter*, or a salt thereof.

10 Claims, 17 Drawing Sheets

(51) Int. Cl.
| | |
|---|---|
| A61K 39/12 | (2006.01) |
| A61K 9/00 | (2006.01) |
| A61K 39/04 | (2006.01) |
| A61K 39/09 | (2006.01) |
| A61K 39/08 | (2006.01) |
| A61K 39/13 | (2006.01) |
| A61K 39/145 | (2006.01) |
| A61K 39/15 | (2006.01) |
| A61K 39/155 | (2006.01) |
| A61K 39/165 | (2006.01) |
| A61K 39/20 | (2006.01) |
| A61K 39/205 | (2006.01) |
| A61K 39/25 | (2006.01) |
| A61K 39/29 | (2006.01) |
| C12N 7/00 | (2006.01) |

(52) U.S. Cl.
CPC ............ A61K 39/205 (2013.01); A61K 39/25 (2013.01); A61K 39/29 (2013.01); A61K 39/292 (2013.01); C12N 7/00 (2013.01); A61K 2039/541 (2013.01); A61K 2039/55572 (2013.01); A61K 2039/575 (2013.01); C12N 2710/16734 (2013.01); C12N 2710/20034 (2013.01); C12N 2720/12334 (2013.01); C12N 2730/10134 (2013.01); C12N 2760/16034 (2013.01); C12N 2760/16134 (2013.01); C12N 2760/16234 (2013.01); C12N 2760/18434 (2013.01); C12N 2760/18734 (2013.01); C12N 2760/20134 (2013.01); C12N 2770/24134 (2013.01); C12N 2770/32434 (2013.01); C12N 2770/32634 (2013.01); C12N 2770/36234 (2013.01)

(56) References Cited

U.S. PATENT DOCUMENTS

| | | |
|---|---|---|
| 2014/0220063 A1 | 8/2014 | Asari et al. |
| 2014/0220079 A1 | 8/2014 | Asari et al. |
| 2014/0234377 A1 | 8/2014 | Okazaki et al. |
| 2016/0206728 A1 | 7/2016 | Kiyotoh et al. |
| 2016/0213773 A1 | 7/2016 | Fukasaka et al. |
| 2016/0228540 A1 | 8/2016 | Kiyotoh et al. |
| 2016/0287687 A1 | 10/2016 | Mahr et al. |
| 2016/0287697 A1 | 10/2016 | Matsushita et al. |
| 2017/0028054 A1 | 2/2017 | Fukasaka et al. |

FOREIGN PATENT DOCUMENTS

| | | |
|---|---|---|
| JP | 2009-242367 A | 10/2009 |
| JP | 2012-82156 A | 4/2012 |
| JP | 2013-527218 A | 6/2013 |
| WO | 96/23002 A1 | 8/1996 |
| WO | 2005/027964 A1 | 3/2005 |
| WO | 2007/068907 A2 | 6/2007 |
| WO | 2009/065415 A1 | 5/2009 |
| WO | 2013/006569 A2 | 1/2013 |

OTHER PUBLICATIONS

European Search Report issued with respect to Application No. 14850476.4, dated Mar. 22, 2017.
European Search Report issued with respect to application No. 14851195.9, dated Mar. 23, 2017.
International Search Report issued with respect to application No. PCT/JP2014/076347, dated Dec. 16, 2014.
International Preliminary Report on Patentability issued with respect to application No. PCT/JP2014/076347, dated Apr. 5, 2016.
International Search Report issued with respect to application No. PCT/JP2014/076349, dated Dec. 16, 2014.
International Preliminary Report on Patentability issued with respect to application No. PCT/JP2014/076349, dated Apr. 5, 2016.
He et al., "Modulation of Mucosal Immune Response by Bacterial Lipopolysaccharide in Nasal Vaccination Models", Journal of Dental Health, 2012, vol. 62, No. 2, pp. 263.
Sapta et al., "Mucosal Adjuvanticity of bacterial lipopolysaccharide in compared with cholera toxin", Proceedings of the Japanese Society for Immunology, 2012, vol. 41, pp. 89.
Office Action from U.S. Appl. No. 14/917,077 dated Jan. 12, 2018.
Office Action issued with respect to European Application No. 14850476.4, dated Dec. 21, 2017.
Arenas et al., "The Role of Bacterial Lipopolysaccharides as Immune Modulator in Vaccine and Drug Development", Endocrine, Metabolic & Immune Disorders—Drug Targets, 2012, 12(3)221-235.
Office Action issued with respect to U.S. Appl. No. 14/917,077, dated Oct. 13, 2016.
Office Action issued with respect to U.S. Appl. No. 14/917,077, dated Apr. 27, 2017.
Hebishima et al., "Oral Administration of Immunopotentiator from Pantoea agglomerans 1 (IP-PA1) Improves the Survival of B16 Melanoma-Inoculated Model Mice", Experimental Animals, vol. 60, No. 2, 2011, pp. 101-109, XP055425351.
Yuki et al., "New Generation of Mucosal Adjuvants for the Induction of Protective Immunity", Reviews in Medical Viro, vol. 13, No. 5, 2003, pp. 293-310, XP009031909.
European Office Action from Application No. 14851195.9 dated Apr. 17, 2018.
Office Action issued in JP 2014-204023, dated Jun. 12, 2018, with English translation.
Gwinn et al., A comparison of non-toxin vaccine adjuvants for their ability to enhance the immunogenicity of nasally-administered anthrax recombinant protective antigen, Vaccine 2013, 31(11):1480-1489.
Hirano et al., "Kinetics of mouse antibody and lymphocyte responses during intranasal vaccination with a lipooligosaccharide-based conjugate vaccine", Immunology Letters 2006, 107:131-139.
Tseng et al., "Effect of lipopolysaccharide on intranasal administration of liposomal Newcastle disease virus vaccine to SPF chickens", Veterinary Immunology and Immunopathology 2009, 131:285-289.
Hebijima et al., Abstract EP-6: "Effect of immune-potentiator from Pantoea aggromelans 1 (IP-PA1) on reduction of Salmonella vaccine reactivity in steroid-administered stress model fown", Abstracts of Annual Meeting of the Japanese Society of Veterinary Science 2009, 147:256.
Office Action issued in JP 2014-204022, dated Jun. 12, 2018, with English translation.
Taniguchi et al., "Identification and Characterization of Lipopolysaccharide in Acetic Acid Bacteria", Anticancer Research 2006, 26: 3997-4002.
Kaminski et al., "Mucosal Adjuvanticity of a Shigella Invasin Complex with DNA-Based Vaccines", Clinical and Vaccine Immunology 2009, pp. 574-586.
Wang et al., "Mechanism of the Effect of LPSp on the Production of Anti-HBs in Mice", Xi Bao Yu Fen Zi Mian Yi Xue Za Zhi 2007.
Office Action issued in RU 2016109368, dated Jul. 12, 2018, with English translation.
Office Action issued in TW 103134468, dated Jul. 4, 2018, with English translation.
Office Action issued in TW 103134466, dated Jul. 25, 2018, with English translation.
Office Action issued in RU 2016109150, dated Jul. 12, 2018, with English translation.

* cited by examiner

MUCOSAL VACCINE COMPOSITION

TECHNICAL FIELD

The present invention relates to a mucosal vaccine composition that is useful as a prophylactic or therapeutic agent for infectious diseases or cancers, and can be administered to an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane. In particular, the present invention relates to a mucosal vaccine composition capable of safely and effectively inducing the systemic immune response and mucosal immune response by being administered to the surface of a mucous membrane together with an antigen, using a specific lipopolysaccharide as an adjuvant.

BACKGROUND ART

As the dosage form of vaccine preparations, most of the commercial products that are currently available are injections. An injectable vaccine induces the blood (systemic) immune response (production of an IgG antibody), but does not induce the immune response (production of an IgA antibody) in mucous membranes, and hence has a problem of difficulty in preventing the infection itself with a pathogen via the mucosal pathway although proliferation of the pathogen after infection can be prevented.

In light of this, recently, vaccination from mucous membranes attracts attention, and among others, development of a mucosal administration (transnasal administration) type vaccine using an influenza virus as an antigen is in the limelight.

A mucosal administration type vaccine is capable of inducing not only the systemic immunity (production of an IgG antibody) but also the mucosal immunity (production of an IgA antibody). The IgA antibody is featured by not distinguishing the type of the pathogen of the objective disease so strictly, and being capable of responding to change in the prevailing type of the pathogen that changes every year, and hence it is considered as being effective for preventing a pandemic.

The transnasal administration type vaccine is in the limelight partly because administration of an antigen to a nasal mucous membrane is not affected by gastric acid and protease, while administration of an antigen to a mucous membrane of a digestive tract is likely to be affected by these, and the affection is difficult to be avoided. Further, on a nasal mucous membrane, there is an antigen recognizing tissue called NALT, and this is also a reason why the transnasal administration type vaccine is effective on the immune response.

However, administration of an antigen to the nasal mucous membrane has a high possibility of a severe side effect such as acute encephalopathy although it is highly effective. Also it has the problems that transnasal administration itself is cumbersome and difficult for the aged, infants and so on, and stable effects cannot be obtained due to physical factors such as a running nose.

On the other hand, the attempt to orally administer an antigen, and following swallowing, to induce the systemic immunity and the mucosal immunity in the mucous membrane of the digestive tract (small intestine) or the like has often been made. The problem in such an attempt lies in how digestion of the antigen by gastric acid and digestion of the antigen by protease are prevented. For solving such a problem, a technique of incorporating a large quantity of an antacid for neutralizing the gastric acid, or a technique for protecting an antigen by a coating technique such as a microsphere have been developed.

However, a technique that has been actually successful is based on live attenuated poliovirus vaccines or live attenuated rotavirus vaccines that are originally highly stable in the gastric acid.

As an example of inducing the mucosal immunity and the systemic immunity in the intraoral mucosal route, the following reports have been made.

Patent Literature 1 proposes an immunogenic composition containing one or more antigens and a Toll-like receptor (TLR) agonist in an oral (for example, sublingual administration) composition, and discloses an influenza antigen as an antigen, and a TLR4 agonist as an adjuvant.

However, the TLR4 agonist in the immunogenic composition proposed in Patent Literature 1 has weak effect in terms of the immune induction, and hence, an adjuvant that is capable of inducing stronger immunity and is safe has been demanded.

Also, Patent Literature 2 proposes a lipopolysaccharide (LPS) derived from *Pantoea* bacteria, and describes that the LPS is safer than conventional LPSs, and the immune reaction is enhanced when it is administered together with an antigen.

Patent Literature 2, however, lacks distinct reference and illustration regarding the use for acquired immunity, and also lacks reference to the optimum ratio of adjuvant/antigen. Further, Patent Literature 2 lacks distinct reference regarding use of an LPS derived from *Pantoea* bacteria as a mucosal vaccine.

Also, Patent Literature 3 proposes a vaccine containing a combination of Poly(I:C) and zymosan as an inactivated antigen of a pathogen, and an immunostimulant (adjuvant), and describes an example of using a lipopolysaccharide (LPS) derived from *Pantoea agglomerans* as an adjuvant, and an influenza virus as a pathogen.

In the example of the vaccine containing a lipopolysaccharide (LPS) derived from *Pantoea agglomerans* described in Patent Literature 3, the vaccine is administered to a nasal mucous membrane, and there is no teaching about administration to a specific mucous membrane such as an intraoral mucous membrane. Generally, it is the common knowledge in the art that the effective adjuvant differs depending on the administration site. Therefore, it is unclear whether a lipopolysaccharide (LPS) derived from *Pantoea agglomerans* is effective in an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane from the example of the vaccine containing a lipopolysaccharide (LPS) derived from *Pantoea agglomerans* described in Patent Literature 3.

CITATION LIST

Patent Literatures

Patent Literature 1: JP 2013-527218 T
Patent Literature 2: JP 4043533 B1
Patent Literature 3: JP 2009-242367 A

SUMMARY OF INVENTION

Technical Problems

In view of the aforementioned situation, it is an object of the present invention to provide a mucosal vaccine composition capable of being administered to an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane, that is safe, useful as a prophylactic or therapeutic agent for infectious diseases and cancers, and is capable of effectively inducing the systemic immune response and mucosal immune response.

Solution to Problems

The present inventors made various investigations for solving the aforementioned problems, and found that it is possible to induce the systemic immune response and mucosal immune response safely and effectively by administering, as an adjuvant, a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas,* and *Enterobacter,* or a salt thereof, together with an antigen, to an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane, in administration to the intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane. These findings have now led to completion of the present invention.

That is, the present invention is a mucosal vaccine composition to be administered to at least one mucous membrane selected from the group consisting of a human or animal intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, and rectal mucous membrane, the mucosal vaccine composition containing at least one antigen, and, as an adjuvant, a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas,* and *Enterobacter,* or a salt thereof.

The mucosal vaccine composition of the present invention is a liquid preparation, a nebular, a semisolid preparation, or a solid preparation. Preferably, the semi-solid preparation and the solid preparation dissolve by a body fluid and/or body temperature.

Preferably, the mucosal vaccine composition of the present invention is a solid preparation that dissolves by a body fluid and/or body temperature.

Preferably, the mucosal vaccine composition of the present invention is used for inducing the humoral immunity.

Preferably, the antigen in the mucosal vaccine composition of the present invention is an antigen derived from an infectious disease or a cancer antigen.

Hereinafter, the present invention will be specifically described.

The mucosal vaccine composition of the present invention contains at least one antigen.

As the antigen used in the present invention, an antigen derived from an infectious disease or a cancer antigen is preferred.

In an antigen derived from an infectious disease, it is required to preliminarily form an antibody by administering a vaccine for the purpose of preventing the disease, so that it is desired to use the present invention. The mucosal vaccine composition of the present invention is suited for activating the humoral immunity.

The antigen derived from an infectious disease is not particularly limited as long as it is an infectious pathogen or an antigen derived from an infectious pathogen.

Non-limiting examples of the diseases developed by an infectious pathogen include viral diseases such as diseases developed by infection with a virus such as an adenovirus, a herpesvirus (e.g., HSV-I, HSV-II, CMV, orVZV), a poxvirus (e.g., smallpox or vaccinia, or an orthopoxvirus such as molluscum contagiosum), a picornavirus (e.g., a rhinovirus or an enterovirus), an orthomyxovirus (e.g., an influenza virus), a paramyxovirus (e.g., a parainfluenza virus, a mumps virus, a measles virus, or a respiratory syncytial virus (RSV)), a coronavirus (e.g., SARS), a papovavirus (for example, a human papilloma virus that causes genital wart, bladder wart vulgaris, or plantar wart), a hepadnavirus (e.g., a hepatitis B virus), a flavivirus (e.g., a hepatitis C virus or a dengue virus), or a retrovirus (e.g., a lentivirus such as HIV), bacterial diseases such as diseases developed by infection with a bacterium such as *Escherichia, Enterobacter, Salmonella, staphylococcus, dysentery bacilli, Listeria, Aerobacter, helicobacter, Klebsiella, Proteus, Pseudomonas, streptococcus, Chlamydia, mycoplasma, pneumococcus, Neisseria, Clostridium, bacillus, Corynebacterium, mycobacterium, Campylobacter, Vibrio, Serratia, Providencia, Chromobacterium, Brucella, Yersinia, Haemophilus,* or *Bordetella,* fungous diseases including, but not limited to, *Chlamydia,* candidiasis, aspergillosis, histoplasmosis, and cryptococcal meningitis, malaria, *Pneumocystis carinii* pneumonia, leishmaniasis, cryptosporidiosis, toxoplasmosis, and *Trypanosoma* infection.

In the present invention, the antigen derived from an infectious disease is preferably at least one selected from the group consisting of an antigen derived from an influenza virus, an antigen derived from human papillomavirus, and an antigen derived from pneumococcus, with an antigen derived from an influenza virus being more preferred.

Here, the influenza virus is an RNA envelope virus belonging to Orthomyxoviridae, and having a particle size of about 100 nm in diameter, and is classified into types A, B and C based on the antigenicity of the internal protein. The influenza virus is composed of a core of ribonucleic acid (RNA) associated with an internal nucleocapsid surrounded by a virus envelope having a lipid bilayer structure or nucleic protein, and an external glycoprotein. The inner layer of the virus envelope is mainly formed of matrix protein, and the outer layer is mostly formed of a lipid substance derived from the host. RNA of the influenza virus has a multipartite structure. Influenza that is pandemic all over the world is caused by an influenza A type virus, and the influenza A type virus has two envelope glycoproteins: hemagglutinin (HA) and neuraminidase (NA), and is classified into 16 subtypes for HA and 9 subtypes for NA depending on the antigenicity.

In the present invention, as the antigen derived from an infectious disease, antigens derived from influenza A type and B type viruses are preferably used. The subtype of the influenza A type and B type viruses is not particularly limited, and may be a subtype that is already isolated, or a subtype that will be isolated in future.

In the present invention, the antigen derived from an influenza virus is not particularly limited as long as it is at least part of various components constituting the influenza virus, and may be a subvirion obtained by digesting a purified viral particle with an organic solvent/surfactant or another reagent so that the lipid envelope is solubilized, or a viral subunit such as HA and NA, or may be a viral whole particle. From the view point of immunogenicity, HA or a viral whole particle is preferred. The viral whole particle is preferably inactivated with formalin or the like.

The method for preparing the aforementioned influenza viral antigen is not particularly limited, and any known method can be used without restriction. One exemplary method includes: infecting a hen egg with a viral strain that is isolated from an animal or a patient infected with influenza, culturing the hen egg by an ordinary method, and preparing an antigen from the purified undiluted viral culture. Also an antigen derived from a virus prepared in cultured cells by genetic engineering may be used.

In the mucosal vaccine composition of the present invention, the antigen is required to be contained in an effective amount. For example, the antigen is preferably contained in an amount of 0.01 to 10000 µg per a single dose in the mucosal vaccine composition of the present invention. If the amount is less than 0.01 µg, the function as a prophylactic or therapeutic agent for infectious diseases or cancers can be insufficient, and if it is more than 10000 µg, a problem regarding the safety can arise. A more preferred lower limit of the antigen content is 0.1 µg, and a more preferred upper limit thereof is 5000 µg.

The "mass of the antigen" used herein refers to the mass of the antigen protein contained in the antigen in the vaccine composition unless otherwise specified. Therefore, when the antigen is a substance derived from an organism such as a virus, the wording means the mass of the whole protein contained in the antigen.

The mucosal vaccine composition of the present invention contains an adjuvant.

As the adjuvant, a toll-like receptor 4 (TLR4) agonist can be recited. In the present invention, as the toll-like receptor 4 (TLR4) agonist, a specific lipopolysaccharide, or a derivative or a salt thereof is used.

The term "lipopolysaccharide" used herein refers to a lipopolysaccharide itself, or may be a derivative of a lipopolysaccharide as far as it has the property of the lipopolysaccharide. The salt used herein may be a salt of any organic acid or inorganic acid, and is preferably a pharmaceutically acceptable salt.

Here, a lipopolysaccharide (hereinafter, also referred to as an LPS) will be described.

An LPS is a composite compound composed of a lipid and a saccharide existing in the outer membrane surrounding peptide glycan of cell walls of gram-negative bacteria such as *Escherichia coli*, *Salmonella typhimurium*, and *Bordetella pertussis*, and is known as an active component of O antigen and endotoxin [J. M. Ghuysen and R. Hakenbeck ed., "New Comprehensive Biochemistry", Vol. 27, Bacterial Cell Wall, p. 18, Elsevier, 1994].

The basic structure of an LPS consists of three components: lipid A having a specific lipid, an oligosaccharide covalently bonded thereto, which is called an R core, and an O-specific polysaccharide ("Nikkei Biotechnology Up-to-date Glossary", p. 431, Nikkei Macgraw-hill, 1985).

The structure of the O-specific polysaccharide is the most diverse in the components, specific for the bacterial species, and shows the activity as a so-called O antigen. Generally, it is characterized by a structure in which oligosaccharides made up of several kinds of monosaccharides are repeated, however, the one composed of identical monosaccharides, or the one not having a repetitive structure is also known.

The mucosal vaccine composition of the present invention contains a lipopolysaccharide derived from a specific gram-negative bacterium or a salt thereof, as an adjuvant. These are contained in many foods and herbal medicines, and hence assured to be safe to the living body, and extracts derived from these bacteria or modified substances thereof can also be used as they are.

Examples of bacteria from which a lipopolysaccharide for use in the adjuvant is derived include *Serratia* (species closely related to *Pantoea*/bread, meat, milk, one species of indigenous bacteria), *Leclercia* (species closely related to *Pantoea*/foods in general (soil bacteria)), *Rahnella* (species closely related to *Pantoea*/one species of indigenous bacteria), *Acidicaldus* (acetic bacteria/fermented food production), *Acidiphilium* (acetic bacteria/fermented food production), *Acidisphaera* (acetic bacteria/fermented food production), *Acidocella* (acetic bacteria/fermented food production), *Acidomonas* (acetic bacteria/fermented food production), *Asaia* (acetic bacteria/fermented food production), *Belnapia* (acetic bacteria/fermented food production), *Craurococcus* (acetic bacteria/fermented food production), *Gluconacetobacter* (acetic bacteria/fermented food production), *Gluconobacter* (acetic bacteria/fermented food production), *Kozakia* (acetic bacteria/fermented food production), *Leahibacter* (acetic bacteria/fermented food production), *Muricoccus* (acetic bacteria/fermented food production), *Neoasaia* (acetic bacteria/fermented food production), *Oleomonas* (acetic bacteria/fermented food production), *Paracraurococcus* (acetic bacteria/fermented food production), *Rhodopila* (acetic bacteria/fermented food production), *Roseococcus* (acetic bacteria/fermented food production), *Rubritepida* (acetic bacteria/fermented food production), *Saccharibacter* (acetic bacteria/fermented food production), *Stella* (acetic bacteria/fermented food production), *Swaminathania* (acetic bacteria/fermented food production), *Teichococcus* (acetic bacteria/fermented food production), *Zavarzinia* (acetic bacteria/fermented food production), *Pseudomonas* (*Pseudomonas* bacteria/beef, egg, meat, fish, vegetable), *Achromobacter* (*Achromobacter* bacteria/fish, meat), *Bacillus* (*Bacillus* bacteria/rice, vegetable), *Methanoculleus* (methane-producing bacteria/methane-producing bacterium parasitizing on animal intestines), *Methanosarcina* (methane-producing bacteria/methane-producing bacterium parasitizing on animal intestines), *Clostridium* (*Clostridium* bacteria/meat, milk, vegetable, canned food), *Micrococcus* (*Actinomycetes*/meat, fish), *Flavobacterium* (*Bacteroides* bacteria/putrefactive bacterium of food), *Pantoea*, *Acetobacter*, *Zymomonas*, *Xanthomonas*, and *Enterobacter*. These are assured to be safe to the living body because these are contained in many foods, or used in the course of producing foods.

Among these, at least one selected from the group consisting of *Serratia*, *Leclercia*, *Rahnella*, *Acidicaldus*, *Acidiphilium*, *Acidisphaera*, *Acidocella*, *Acidomonas*, *Asaia*, *Belnapia*, *Craurococcus*, *Gluconacetobacter*, *Gluconobacter*, *Kozakia*, *Leahibacter*, *Muricoccus*, *Neoasaia*, *Oleomonas*, *Paracraurococcus*, *Rhodopila*, *Roseococcus*, *Rubritepida*, *Saccharibacter*, *Stella*, *Swaminathania*,

*Teichococcus, Zavarzinia, Pantoea, Acetobacter, Zymomonas, Xanthomonas,* and *Enterobacter* is preferred.

More preferably, the gram-negative bacterium is at least one selected from the group consisting of *Pantoea, Acetobacter, Zymomonas, Xanthomonas,* and *Enterobacter.* In particular, a lipopolysaccharide derived from *Pantoea* is currently used as a health food, and is particularly effective when it is orally administered. Extracts derived from these bacteria or modified substances thereof can also be used as they are.

When a lipopolysaccharide derived from the gram-negative bacterium or a salt thereof is used, it is generally necessary to take the safety of the living body into account, and a modified substance may be used to detoxify the same.

As the toll-like receptor 4 (TLR4) agonist, a derivative of the aforementioned specific lipopolysaccharide, for example, lipid A from which a polysaccharide moiety is removed or monophosphoryl lipid A, 3-deacylated NFL and so on are recited, or the agonist may be a salt.

The lipid A from which a polysaccharide moiety of a lipopolysaccharide is removed can be an isolate derived from the specific gram-negative bacterium, or can be a synthetic product having the same structure as the isolate derived from the gram-negative bacterium.

As the modified substance of the lipid A, dephosphorylated monophosphoryl lipid (MPL) or a salt thereof is preferably used. The monophosphoryl lipid used herein may be monophosphoryl lipid itself, and a derivative thereof as far as the property is possessed. In particular, 3-deacylated monophosphoryl lipid (3D-MPL) that has already been proven as an adjuvant in medical use, or synthetic glucopyranosyl lipid that is not deacylated, proposed in US Patent Application No. 2010/0310602 is preferred from the view point of safety in a living body.

Also as the monophosphoryl lipid, the one derived from *Salmonella typhimurium* having safety and precedent use is preferably used.

In the present invention, an LPS derived from *Pantoea agglomerans* is further preferably used. Among others, the LPS derived from *Pantoea agglomerans* is preferably an LPS derived from *Pantoea agglomerans* having a molecular weight determined by the SDS-PAGE method using protein markers of 5000±3000, preferably 5000±2000. The molecular weight used herein is measured by the position of the stained band by the SDS-PAGE method using protein markers, and the details will be described later.

The LPS derived from *Pantoea agglomerans* that is also preferably used in the present invention is a lipopolysaccharide wherein the O-antigen moiety is formed of a repeating structure of rhamnose and glucose.

The LPS derived from *Pantoea agglomerans* can be produced by culturing *Pantoea agglomerans* by an ordinary method, collecting the bacterial cells from the culture medium, and purifying the collected bacterial cells according to a known method.

The molecular weight of the LPS derived from *Pantoea agglomerans* can be measured in the following manner.

That is, for an LPS derived from *Pantoea agglomerans* prepared as a blend, or for an LPS derived from *Pantoea agglomerans* extracted and purified from a vaccine composition by an appropriate method, the molecular weight can be determined in the following manner.

An LPS derived from *Pantoea agglomerans* is dissolved in distilled water to prepare a 1 mg/mL solution, equivalent amounts of the solution and Sample buffer solution 2ME+ (available from WAKO) are mixed, and the mixture is dipped in a boiling water bath for 5 minutes, and then immediately dipped in ice water and rapidly cooled.

A slab gel electrophoresis tank (available from Marisol) is filled with a running buffer (available from ATTO), 20% polyacrylamide gel is fixed in the electrophoresis tank, each 10 μL of sample is put into a sample groove, and running is continued for at least one hour at a voltage of 100 V until the pigment is eluted from the gel. After end of the running, silver staining is conducted with a silver staining kit 161-0443 (available from Bio-Rad) at room temperature, and the behavior is checked.

In the mucosal vaccine composition of the present invention, the content (mass) of the adjuvant is preferably set so that it is in the range of 0.002 to 500 as a rate with respect to the mass of the vaccine antigen of the mucosal vaccine composition of the present invention (total mass of adjuvant/total mass of antigen). If it is less than 0.002, a sufficient function as a prophylactic or therapeutic agent for infectious diseases or cancers cannot be obtained, whereas if it is more than 500, the problem of safety can arise. A more preferred lower limit of the rate is 0.01, and a more preferred upper limit thereof is 100.

Also, in the mucosal vaccine composition of the present invention, as the adjuvant, those described above and a different conventionally known adjuvant may be used in combination as long as a specific lipopolysaccharide derived from a gram-negative bacterium or a salt thereof is contained.

The mucosal vaccine composition of the present invention can be prepared by adding other ingredients (e.g., phosphate buffer solution) as needed to the aforementioned antigen and adjuvant, and stirring and mixing them by a known method, or further heating, cooling, or drying without heating as needed by a known method.

Also, it is possible to prepare a liquid preparation, a semisolid preparation, a solid preparation, or a nebular by using the mucosal vaccine composition of the present invention. Besides the aforementioned materials, an excipient, a binder, a flavor, a corrigent, a sweetener, a coloring agent, an antiseptic, an antioxidant, a stabilizer, a surfactant and the like may be appropriately used as desired.

These materials are not particularly limited, and those conventionally known can be used.

The mucosal vaccine composition of the present invention is preferably a liquid preparation, a nebular, a semisolid preparation, or a solid preparation. As will be described later, when the mucosal vaccine composition of the present invention is a liquid preparation, a nebular, a semisolid preparation or a solid preparation, it can be suitably administered to the surface of a human or animal mucous membrane.

Since the mucosal vaccine composition of the present invention is administered to the surface of a human or animal mucous membrane, the semi-solid preparation and the solid preparation preferably dissolve by a body fluid and/or body temperature.

More preferably, since low water content is preferred during storage from the view point of ensuring the safety of the antigen, the mucosal vaccine composition of the present invention is preferably a solid preparation that is in a dry state during storage, and dissolves by a body fluid and/or body temperature after administration to the surface of a mucous membrane. The term "low water content" in this context means that the water content in the total weight of the mucosal vaccine composition of the present invention is preferably less than or equal to 20% by weight, more preferably less than or equal to 10% by weight.

The "water content" in this context is determined according to the first method in Loss on Drying Test, General Tests, The Japanese Pharmacopoeia, Sixteenth Edition. That is, it is determined by the rate of loss in weight when a test piece of the mucosal vaccine composition of the present invention is heated for 3 hours at 105° C.

For realizing such characteristics of the solid preparation, it is preferred to select a material that dissolves by a body fluid and/or body temperature as a material for the mucosal vaccine composition of the present invention. As such a material, for example, it is preferred to select an LPS derived from *Pantoea agglomerans* having high water solubility as the adjuvant, and it is preferred to select a polymer having the physical property of dissolving by a body fluid and/or body temperature as the excipient. By employing such a solid preparation, the preparation can be administered intraorally easily without necessity of a special device.

Here, examples of the solid preparation include tablets, coated tablets, powders, granules, fine granules, disintegrating tablets, patches, rapid soluble tablets, and films, and the solid preparation is not particularly limited as long as it is solid and administered to the surface of a mucous membrane. The solid preparation is preferably a film preparation, a disintegrating tablet or a rapid soluble tablet.

The semi-solid preparation is preferably a gel, an ointment, a cream or a syrup.

The mucosal vaccine composition of the present invention is administered to at least one mucous membrane selected from the group consisting of a human or animal (mammal, avian or the like) intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane, and is preferably administered to an intraoral mucous membrane. While an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane has been generally considered as being difficult to activate the immunity, the mucosal vaccine composition of the present invention, which contains the aforementioned specific adjuvant together with at least one antigen, can effectively induce the systemic immune response and mucosal immune response even when it is administered to the intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane. Also, by selecting an intraoral mucous membrane as an administration route, influence of gastric acid or influence of protease is avoided unlike the case where an antigen is administered to the mucous membrane of the digestive tract, and also the possibility of a severe side effect such as acute encephalopathy is avoided unlike the case where an antigen is administered transnasally. Therefore, easy administration to the aged, infants and so on is achieved, and stable effects are not interfered by physical factors such as a running nose.

The administration method of the mucosal vaccine composition of the present invention is as described above. The dose thereof is determined in consideration of the animal species, and age, sex, body weight and the like of the subject. For example, when HA is used as an antigen, usually 0.1 µg to 50 µg can be administered once or two or more times. Preferably, it is administered two or more times, and in this case, it is preferably administered at intervals of one to four weeks.

Advantageous Effects of Invention

Since the mucosal vaccine composition of the present invention contains the aforementioned specific adjuvant together with at least one antigen, it can induce the humoral immunity, for example, the systemic immune response and mucosal immune response safely and effectively by being administered to the intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane.

DESCRIPTION OF EMBODIMENTS

Figure 1:
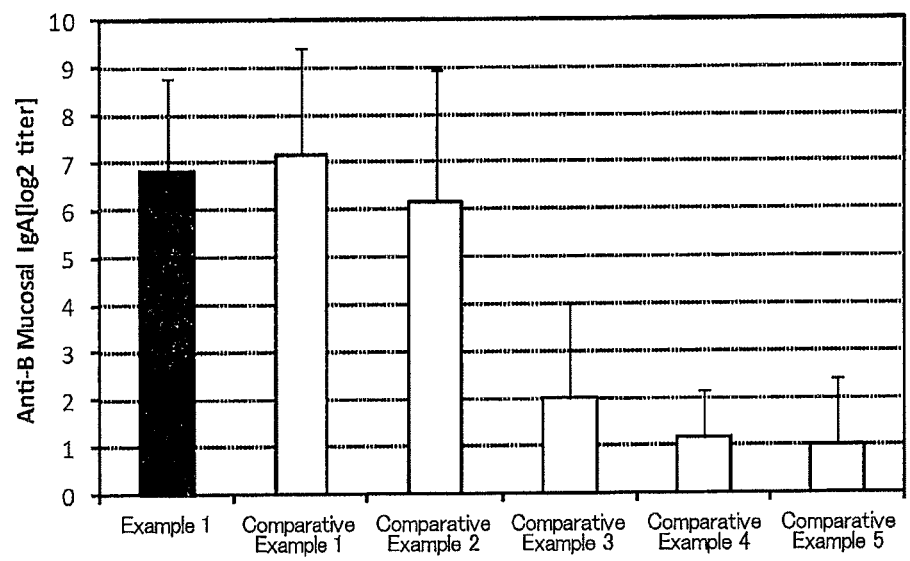
FIG. 1 is a graph showing results of influenza HA (type B)-specific IgA titers in a mouse nasal cavity washing liquid in Example 1, and Comparative Examples 1 to 5.
Figure 2:
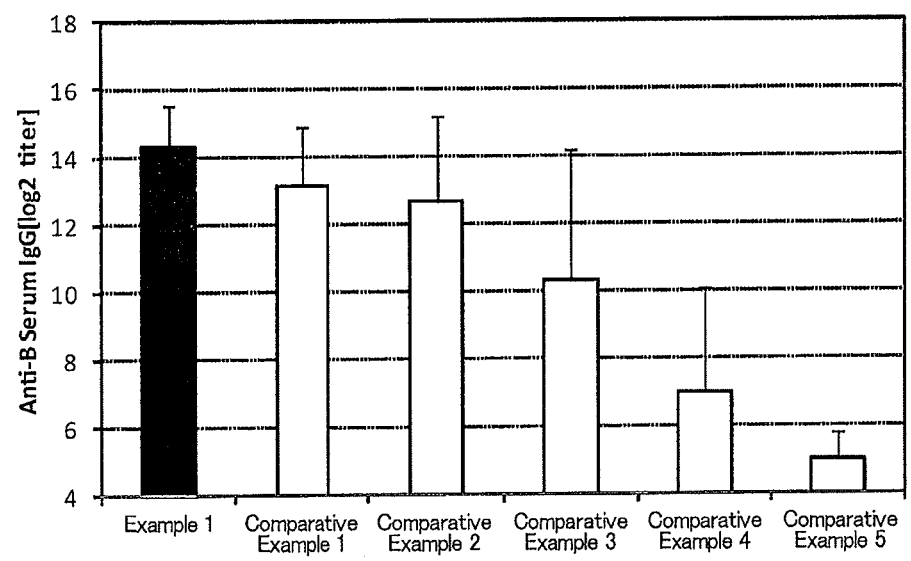
FIG. 2 is a graph showing results of influenza HA (type B)-specific IgG titers in a mouse serum in Example 1, and Comparative Examples 1 to 5.
Figure 3:
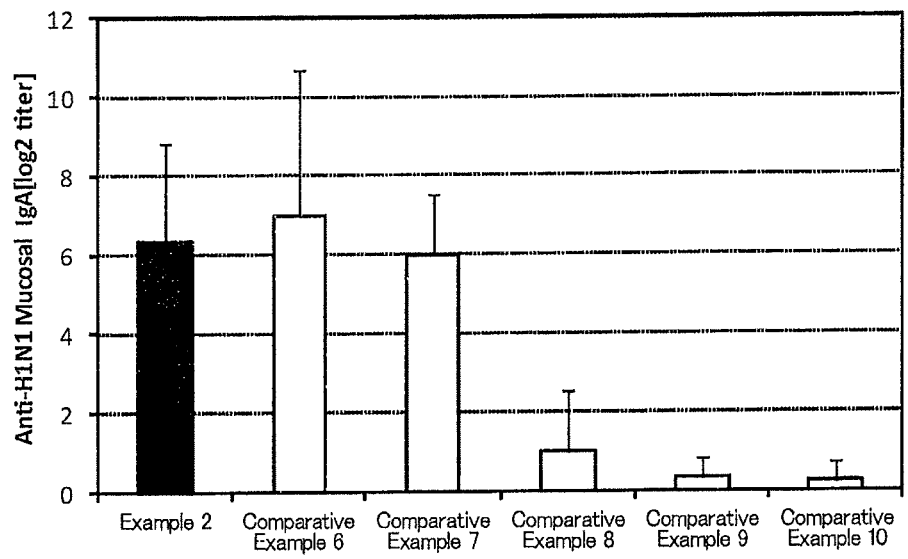
FIG. 3 is a graph showing results of influenza HA (H1N1)-specific IgA titers in a mouse nasal cavity washing liquid in Example 2, and Comparative Examples 6 to 10.
Figure 4:
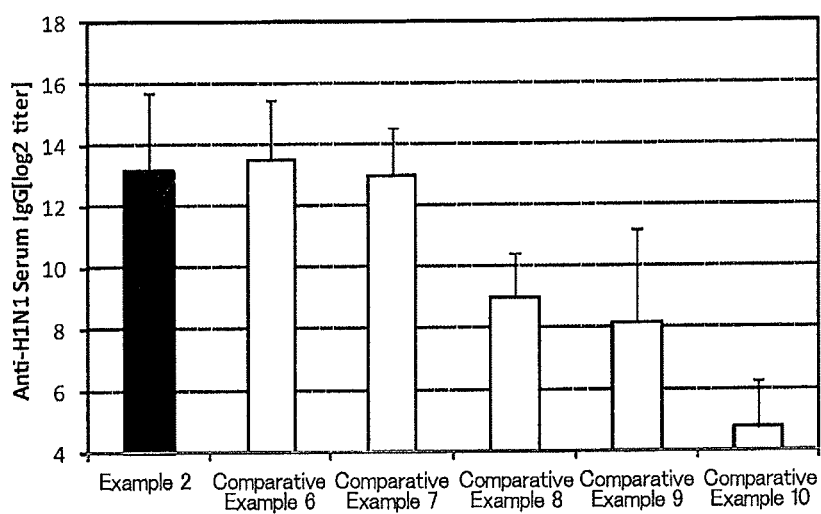
FIG. 4 is a graph showing results of influenza HA (H1N1)-specific IgG titers in a mouse serum in Example 2, and Comparative Examples 6 to 10.

The present invention will be described in more detail with reference to the following examples, but is not limited to these examples.

Example 1

To 2.25 μL (445 μg/mL) of an influenza vaccine antigen-containing solution (B/Wisconsin/1/2010, available from The Research Foundation for Microbial Diseases of Osaka University), and 5 μL (2 mg/mL) of a solution of a lipopolysaccharide derived from *Pantoea agglomerans* (available from Nacalai Tesque), a phosphate buffer (available from Nacalai Tesque) was added to prepare 300 μL of a mucosal vaccine composition.

Six mice (female BALB/C mice aged 8 weeks, Japan SLC, Inc.) were anesthetized, and 30 μL of the prepared vaccine composition was sublingually administered to each mouse. After one week from the administration, the mice were anesthetized again, and 30 μL of the prepared vaccine composition was sublingually administered to each mouse. After one week from the second administration, a serum and a nasal cavity washing liquid of each mouse were collected, and an influenza HA (type B)-specific IgG titer in a serum and an influenza HA (type B)-specific IgA titer in a nasal cavity washing liquid were determined by the ELISA method. Specific determination methods will be described later.

Comparative Examples 1 to 5

A mucosal vaccine composition was prepared in the same manner as in Example 1 except that, in place of a lipopolysaccharide derived from *Pantoea agglomerans*, a lipopolysaccharide derived from *Escherichia coli* (available from WAKO) was used in Comparative Example 1, a lipopolysaccharide derived from *Salmonella typhimurium* (available from WAKO) was used in Comparative Example 2, glucopyranosyl lipid (MPLAs, available from InvivoGen) was used in Comparative Example 3, and Imiquimod (available from InvivoGen) was used in Comparative Example 4, and the test was conducted in the same manner as in Example 1 with the administration amount shown in Table 1. In Comparative Example 5, only a phosphate buffer (available from Nacalai Tesque) was administered to mice while a vaccine antigen and an adjuvant were not added.

TABLE 1

| No. | Vaccine antigen | | Adjuvant | | | Administration route |
|---|---|---|---|---|---|---|
| | Species | Amount [μg/mouse/dose] | Substance name | Ligand | Amount [μg/mouse/dose] | |
| Example 1 | B/Wisconsin/1/2010 | 0.1 | LPS derived from *Pantoea agglomerans* | TLR4 | 1 | Sublingual |
| Comparative Example 1 | B/Wisconsin/1/2010 | 0.1 | LPS derived from *Escherichia coli* | TLR4 | 1 | Sublingual |
| Comparative Example 2 | B/Wisconsin/1/2010 | 0.1 | LPS derived from *Salmonella typhimurium* | TLR4 | 1 | Sublingual |
| Comparative Example 3 | B/Wisconsin/1/2010 | 0.1 | Glucopyranosyl lipid | TLR4 | 1 | Sublingual |
| Comparative Example 4 | B/Wisconsin/1/2010 | 0.1 | Imiquimod | TLR7 | 1 | Sublingual |
| Comparative Example 5 | — | — | — | — | — | Sublingual |

Example 2

To 1.25 µL (801 µg/mL) of an influenza vaccine antigen-containing solution (A/California/07/2009 (H1N1), available from The Research Foundation for Microbial Diseases of Osaka University), and 5 µL (2 mg/mL) of a solution of a lipopolysaccharide derived from *Pantoea agglomerans* (available from Nacalai Tesque), a phosphate buffer (available from Nacalai Tesque) was added to prepare 300 µL of a mucosal vaccine composition.

Six mice (female BALB/C mice aged 8 weeks, Japan SLC, Inc.) were anesthetized, and 30 µL of the prepared mucosal vaccine composition was sublingually administered to each mouse. After one week from the administration, the mice were anesthetized again, and 30 µL of the prepared mucosal vaccine composition was sublingually administered to each mouse. After one week from the second administration, a serum and a nasal cavity washing liquid of each mouse were collected, and an influenza HA (H1N1)-specific IgG titer in a serum and an influenza HA (H1N1)-specific IgA titer in a nasal cavity washing liquid were determined by the ELISA method. Specific determination methods will be described later.

Comparative Examples 6 to 10

A mucosal vaccine composition was prepared in the same manner as in Example 2 except that, in place of a lipopolysaccharide derived from *Pantoea agglomerans*, a lipopolysaccharide derived from *Escherichia coli* (available from WAKO) was used in Comparative Example 6, a lipopolysaccharide derived from *Salmonella typhimurium* (available from WAKO) was used in Comparative Example 7, glucopyranosyl lipid (MPLAs, available from InvivoGen) was used in Comparative Example 8, and Imiquimod (available from InvivoGen) was used in Comparative Example 9, and the test was conducted in the same manner as in Example 2 with the administration amount shown in Table 2. In Comparative Example 10, only a phosphate buffer (available from Nacalai Tesque) was administered to mice while a vaccine antigen and an adjuvant were not added.

Reference Example 1

A sample containing the same antigen and adjuvant as those in the sample administered in Example 1, and having the same (antigen/adjuvant) as Example 1 was prepared, and the safety of the sample was evaluated. To be more specific, to 225 µL (445 µg/mL) of an influenza vaccine antigen-containing solution (B/Wisconsin/1/2010, available from The Research Foundation for Microbial Diseases of Osaka University), and 500 µL (2 mg/mL) of a solution of a lipopolysaccharide derived from *Pantoea agglomerans* (available from Nacalai Tesque), a phosphate buffer (available from Nacalai Tesque) was added to prepare 1000 µL of a vaccine composition.

Eight mice (female BALB/C mice aged 8 weeks, Japan SLC, Inc.) were anesthetized, and 100 µL of the prepared vaccine composition was subcutaneously administered to each mouse. The mice were followed up to 72 hours from the administration, and the survival rate was observed.

Reference Comparative Examples 1 and 2

A vaccine composition was prepared in the same manner as in Reference Example 1 except that, in place of a lipopolysaccharide derived from *Pantoea agglomerans*, a lipopolysaccharide derived from *Escherichia coli* (available from WAKO) was used in Reference Comparative Example 1, and a lipopolysaccharide derived from *Salmonella typhimurium* (available from WAKO) was used in Reference Comparative Example 2, and the test was conducted in the same manner as in Reference Example 1 with the administration amount shown in Table 3.

TABLE 2

| No. | Vaccine antigen Species | Amount [µg/mouse/dose] | Adjuvant Substance name | Ligand | Amount [µg/mouse/dose] | Administration route |
|---|---|---|---|---|---|---|
| Example 2 | A/California/07/2009(H1N1) | 0.1 | LPS derived from *Pantoea agglomerans* | TLR4 | 1 | Sublingual |
| Comparative Example 6 | A/California/07/2009(H1N1) | 0.1 | LPS derived from *Escherichia coli* | TLR4 | 1 | Sublingual |
| Comparative Example 7 | A/California/07/2009(H1N1) | 0.1 | LPS derived from *Salmonella typhimurium* | TLR4 | 1 | Sublingual |
| Comparative Example 8 | A/California/07/2009(H1N1) | 0.1 | Glucopyranosyl lipid | TLR4 | 1 | Sublingual |
| Comparative Example 9 | A/California/07/2009(H1N1) | 0.1 | Imiquimod | TLR7 | 1 | Sublingual |
| Comparative Example 10 | — | — | — | — | — | Sublingual |

TABLE 3

| | Vaccine antigen | | Adjuvant | | | |
|---|---|---|---|---|---|---|
| No. | Species | Amount [μg/mouse/dose] | Substance name | Ligand | Amount [μg/mouse/dose] | Administration route |
| Reference Example 1 | B/Wisconsin/1/2010 | 10 | LPS derived from *Pantoea agglomerans* | TLR4 | 100 | Subcutaneous |
| Reference Comparative Example 1 | B/Wisconsin/1/2010 | 10 | LPS derived from *Escherichia coli* | TLR4 | 100 | Subcutaneous |
| Reference Comparative Example 2 | B/Wisconsin/1/2010 | 10 | LPS derived from *Salmonella typhimurium* | TLR4 | 100 | Subcutaneous |

Examples 3 and 4

To 2.5 μL (801 μg/mL) of an influenza vaccine antigen-containing solution (A/California/07/2009 (H1N1), available from The Research Foundation for Microbial Diseases of Osaka University), and 10 μL (2 mg/mL) of a solution of a lipopolysaccharide derived from *Pantoea agglomerans* (available from Nacalai Tesque), 45 mg of hydroxypropylcellulose (HPC-SSL, available from Nippon Soda Co., Ltd.) as a base material was added, and a phosphate buffer (available from Nacalai Tesque) was added and mixed uniformly to give 500 mg of a mixture. Then, the mixture was dispensed by 25 mg, and freeze-dried to prepare rapid soluble tablets in Example 3, and was dried under reduced pressure to prepare film preparations in Example 4.

Six mice (female BALB/C mice aged 8 weeks, Japan SLC, Inc.) were anesthetized, and the prepared rapid soluble tablet or film preparation was sublingually administered to each mouse. After one week from the administration, the mice were anesthetized again, and the prepared rapid soluble tablet or film preparation was sublingually administered to each mouse. After one week from the second administration, a serum and a nasal cavity washing liquid of each mouse were collected, and an influenza HA (H1N1)-specific IgG titer in a serum and an influenza HA (H1N1)-specific IgA titer in a nasal cavity washing liquid were determined by the ELISA method. Specific determination methods will be described later. In Table 4, results of Example 2 and Comparative Example 10 are also shown.

Example 5

To 87 μL (1150 μg/mL) of a pneumococcal capsular polysaccharide-containing solution (PNEUMOVAX NP, MSD K.K.), and 2.5 μL (2 mg/mL) of a solution of a lipopolysaccharide derived from *Pantoea agglomerans* (available from Nacalai Tesque), a phosphate buffer (available from Nacalai Tesque) was added to prepare 100 μL of a mucosal vaccine composition.

Four mice (female BALB/C mice aged 8 weeks, Japan SLC, Inc.) were anesthetized, and 20 μL of the prepared mucosal vaccine composition was sublingually administered to each mouse. After one week from the administration, the mice were anesthetized again, and 20 μL of the prepared mucosal vaccine composition was sublingually administered to each mouse. After one week from the second administration, a serum and a nasal cavity washing liquid of each mouse were collected, and a pneumococcal capsular polysaccharide-specific IgG titer in a serum and a pneumococcal capsular polysaccharide-specific IgA titer in a nasal cavity washing liquid were determined by the ELISA method. Specific determination methods will be described later.

Comparative Examples 11 and 12

A mucosal vaccine composition was prepared in the same manner as in Example 5 except that, in place of a lipopolysaccharide derived from *Pantoea agglomerans*, glucopyranosyl lipid (MPLAs, available from InvivoGen) was used in Comparative Example 11, and the test was conducted in the same manner as in Example 5 with the administration amount shown in Table 5. In Comparative Example 12, only a phosphate buffer (available from Nacalai Tesque) was administered to mice while a vaccine antigen and an adjuvant were not added.

TABLE 4

| | Vaccine antigen | | Adjuvant | | | | |
|---|---|---|---|---|---|---|---|
| No. | Species | Amount [μg/mouse/dose] | Substance name | Ligand | Amount [μg/mouse/dose] | Administration route | Note |
| Example 3 | A/California/07/2009(H1N1) | 0.1 | LPS derived from *Pantoea agglomerans* | TLR4 | 1 | Sublingual | Dry preparation |
| Example 4 | A/California/07/2009(H1N1) | 0.1 | LPS derived from *Pantoea agglomerans* | TLR4 | 1 | Sublingual | Film |
| Example 2 | A/California/07/2009(H1N1) | 0.1 | LPS derived from *Pantoea agglomerans* | TLR4 | 1 | Sublingual | Liquid |
| Comparative Example 10 | — | — | — | — | — | Sublingual | — |

TABLE 5

| No. | Vaccine antigen | | Adjuvant | | | Administration route |
|---|---|---|---|---|---|---|
| | Species | Amount [μg/mouse/dose] | Substance name | Ligand | Amount [μg/mouse/dose] | |
| Example 5 | Pneumococcal capsular polysaccharide Pneumovax NP | 20 | LPS derived from *Pantoea agglomerans* | TLR4 | 1 | Sublingual |
| Comparative Example 11 | Pneumococcal capsular polysaccharide Pneumovax NP | 20 | Glucopyranosyl lipid | TLR4 | 1 | Sublingual |
| Comparative Example 12 | — | — | — | — | — | Sublingual |

Example 6

To 61 μL (820 μg/mL) of an HPV16 recombinant protein-containing solution (HPV16, available from PROSPEC), and 2.5 μL (2 mg/mL) of a solution of a lipopolysaccharide derived from *Pantoea agglomerans* (available from Nacalai Tesque), a phosphate buffer (available from Nacalai Tesque) was added to prepare 100 μL of a mucosal vaccine composition.

Four mice (female BALB/C mice aged 8 weeks, Japan SLC, Inc.) were anesthetized, and 20 μL of the prepared mucosal vaccine composition was sublingually administered to each mouse. After one week from the administration, the mice were anesthetized again, and 20 μL of the prepared mucosal vaccine composition was sublingually administered to each mouse. After one week from the second administration, a serum and a nasal cavity washing liquid of each mouse were collected, and an HPV16-specific IgG titer in a serum and an HPV16-specific IgA titer in a nasal cavity washing liquid were determined by the ELISA method. Specific determination methods will be described later.

Comparative Examples 13 and 14

A mucosal vaccine composition was prepared in the same manner as in Example 6 except that, in place of a lipopolysaccharide derived from *Pantoea agglomerans*, glucopyranosyl lipid (MPLAs, available from InvivoGen) was used in Comparative Example 13, and the test was conducted in the same manner as in Example 6 with the administration amount shown in Table 6. In Comparative Example 14, only a phosphate buffer (available from Nacalai Tesque) was administered to mice while a vaccine antigen and an adjuvant were not added.

Examples 7 and 8

To 174 μL (1150 μg/mL) of a pneumococcal capsular polysaccharide-containing solution (PNEUMOVAX NP, available from MSD K.K.), and 5 μL (2 mg/mL) of a solution of a lipopolysaccharide derived from *Pantoea agglomerans* (available from Nacalai Tesque), 22.5 mg of hydroxypropylcellulose (HPC-SSL, available from Nippon Soda Co., Ltd.) was added as a base material, and a phosphate buffer (available from Nacalai Tesque) was added and mixed uniformly to give 250 mg of a mixture. Then, the mixture was dispensed by 25 mg, and freeze-dried to prepare rapid soluble tablets in Example 7, and was dried under reduced pressure to prepare film preparations in Example 8.

Four mice (female BALB/C mice aged 8 weeks, Japan SLC, Inc.) were anesthetized, and the prepared rapid soluble tablet or film preparation was sublingually administered to each mouse. After one week from the administration, the mice were anesthetized again, and the prepared rapid soluble tablet or film preparation was sublingually administered to each mouse. After one week from the second administration, a serum and a nasal cavity washing liquid of each mouse were collected, and a PNEUMOVAX NP-specific IgG titer in a serum and a PNEUMOVAX NP-specific IgA titer in a nasal cavity washing liquid were determined by the ELISA method. Specific determination methods will be described later. In Table 7, results of Example 5 and Comparative Example 12 are also shown.

TABLE 6

| No. | Vaccine antige | | Adjuvant | | | Administration route |
|---|---|---|---|---|---|---|
| | Species | Amount [μg/mouse/dose] | Substance name | Ligand | Amount [μg/mouse/dose] | |
| Example 6 | HPV16 recombinant protein | 10 | LPS derived from *Pantoea agglomerans* | TLR4 | 1 | Sublingual |
| Comparative Example 13 | HPV16 recombinant protein | 10 | Glucopyranosyl lipid | TLR4 | 1 | Sublingual |
| Comparative Example 14 | — | — | — | — | — | Sublingual |

TABLE 7

| No. | Vaccine antigen | | Adjuvant | | | Administration route | Note |
|---|---|---|---|---|---|---|---|
| | Species | Amount [μg/mouse/dose] | Substance name | Ligand | Amount [μg/mouse/dose] | | |
| Example 7 | Pneumococcal capsular polysaccharide Pneumovax NP | 20 | LPS derived from *Pantoea agglomerans* | TLR4 | 1 | Sublingual | Dry preparation |
| Example 8 | Pneumococcal capsular polysaccharide Pneumovax NP | 20 | LPS derived from *Pantoea agglomerans* | TLR4 | 1 | Sublingual | Flm |
| Example 5 | Pneumococcal capsular polysaccharide Pneumovax NP | 20 | LPS derived from *Pantoea agglomerans* | TLR4 | 1 | Sublingual | Liquid |
| Comparative Example 12 | — | — | — | — | — | Sublingual | — |

Examples 9 and 10

To 122 μL (820 μg/mL) of an HPV16 recombinant protein-containing solution (HPV16, available from PROSPEC), and 5 μL (2 mg/mL) of a solution of a lipopolysaccharide derived from *Pantoea agglomerans* (available from Nacalai Tesque), 22.5 mg of hydroxypropylcellulose (HPC-SSL, available from Nippon Soda Co., Ltd.) was added as a base material, and a phosphate buffer (available from Nacalai Tesque) was added and mixed uniformly to give 250 mg of a mixture. Then, the mixture was dispensed by 25 mg, and freeze-dried to prepare rapid soluble tablets in Example 9, and was dried under reduced pressure to prepare film preparations in Example 10.

Four mice (female BALB/C mice aged 8 weeks, Japan SLC, Inc.) were anesthetized, and the prepared rapid soluble tablet or film preparation was sublingually administered to each mouse. After one week from the administration, the mice were anesthetized again, and the prepared rapid soluble tablet or film preparation was sublingually administered to each mouse. After one week from the second administration, a serum and a nasal cavity washing liquid of each mouse were collected, and an HPV16-specific IgG titer in a serum and an HPV16-specific IgA titer in a nasal cavity washing liquid were determined by the ELISA method. Specific determination methods will be described later. In Table 8, results of Example 6 and Comparative Example 14 are also shown.

Four mice (female BALB/C mice aged 8 weeks, Japan SLC, Inc.) were anesthetized, and the prepared rapid soluble tablet was sublingually administered to each mouse. After one week from the administration, the mice were anesthetized again, and the prepared rapid soluble tablet was sublingually administered to each mouse. After one week from the second administration, a serum and a nasal cavity washing liquid of each mouse were collected, and an attenuated live rotavirus-specific IgG titer in a serum and an attenuated live rotavirus-specific IgA titer in a nasal cavity washing liquid were determined by the ELISA method.

Examples 12 to 22

A rapid soluble tablet was prepared in the same manner as in Example 11 by using an inactivated poliovirus-containing solution (IMOVAX POLIO subcutaneous, available from Sanofi K.K.) in Example 12, an inactivated hepatitis A virus-containing solution (Aimmugen, available from KAKETSUKEN) in Example 13, an inactivated Japanese encephalitis virus-containing solution (ENCEVAC for subcutaneous injection, available from KAKETSUKEN) in Example 14, an attenuated live mumps virus-containing solution (mumps live vaccine, available from KITASATO DAIICHISANKYO VACCINE CO., LTD.) in Example 15, an attenuated live measles virus-containing solution (measles live vaccine, available from KITASATO DAIICHISANKYO VACCINE CO., LTD.) in Example 16, an

TABLE 8

| No. | Vaccine antigen | | Adjuvant | | | Administration route | Note |
|---|---|---|---|---|---|---|---|
| | Species | Amount [μg/mouse/dose] | Substance name | Ligand | Amount [μg/mouse/dose] | | |
| Example 9 | HPV16 recombinant protein | 10 | LPS derived from *Pantoea agglomerans* | TLR4 | 1 | Sublingual | Dry preparation |
| Example 10 | HPV16 recombinant protein | 10 | LPS derived from *Pantoea agglomerans* | TLR4 | 1 | Sublingual | Film |
| Example 6 | HPV16 recombinant protein | 10 | LPS derived from *Pantoea agglomerans* | TLR4 | 1 | Sublingual | Liquid |
| Comparative Example 14 | — | — | — | — | — | Sublingual | — |

Example 11

To 1000 μL of an attenuated live rotavirus-containing solution (ROTATEQ mixture for internal use, available from MSD K.K.), and 5 μL (2 mg/mL) of a solution of a lipopolysaccharide derived from *Pantoea agglomerans* (available from Nacalai Tesque), 22.5 mg of hydroxypropylcellulose (HPC-SSL, available from Nippon Soda Co., Ltd.) was added as a base material to give 1005 μL of a mixture. Then, the mixture was dispensed by 100 μL, and freeze-dried to prepare rapid soluble tablets.

attenuated live rubella virus-containing solution (dry attenuated live rubella vaccine, available from KITASATO DAIICHISANKYO VACCINE CO., LTD.) in Example 17, a tetanus toxoid conjugate Haemophilus influenzae type b polysaccharide-containing solution (ActHIB, available from Sanofi K.K.) in Example 18, a recombinant HBs antigen protein-containing solution (Bimmugen, available from KAKETSUKEN) in Example 19, an attenuated live yellow fever virus-containing solution (yellow fever vaccine, available from Sanofi K.K.) in Example 20, a tetanus toxoid-containing solution (tetanus toxoid, available from DENKA SEIKEN CO., LTD.) in Example 21, and an attenuated live chickenpox virus-containing solution (dry attenuated live chickenpox vaccine, available from The Research Foundation for Microbial Diseases of Osaka University) in Example 22. Also immunological experiments are conducted as described in Example 12.

Example 23

To 300 μL of a live BCG-containing solution (dry BCG vaccine, available from Japan BCG Laboratory), and 5 μL (2 mg/mL) of a solution of a lipopolysaccharide derived from *Pantoea agglomerans* (available from Nacalai Tesque), 22.5 mg of hydroxypropylcellulose (HPC-SSL, available from Nippon Soda Co., Ltd.) was added as a base material to give 305 μL of a mixture. Then, the mixture was dispensed by 30 μL, and freeze-dried to prepare rapid soluble tablets.

Four mice (female BALB/C mice aged 8 weeks, Japan SLC, Inc.) were anesthetized, and the prepared rapid soluble tablet was sublingually administered to each mouse. After one week from the administration, the mice were anesthetized again, and the prepared rapid soluble tablet was sublingually administered to each mouse. After one week from the second administration, a serum and a nasal cavity washing liquid of each mouse were collected, and a live BCG-specific IgG titer in a serum and an attenuated live BCG-specific IgA titer in a nasal cavity washing liquid were determined by the ELISA method.

Example 24

To 2000 μL of an inactivated rabies virus-containing solution (tissue-cultured inactivated rabies vaccine, available from KAKETSUKEN), and 5 μL (2 mg/mL) of a solution of a lipopolysaccharide derived from *Pantoea agglomerans* (available from Nacalai Tesque), 22.5 mg of hydroxypropylcellulose (HPC-SSL, available from Nippon Soda Co., Ltd.) was added as a base material to give 2005 μL of a mixture. Then, the mixture was dispensed by 200 μL, and freeze-dried to prepare rapid soluble tablets.

Four mice (female BALE/C mice aged 8 weeks, Japan SLC, Inc.) were anesthetized, and the prepared rapid soluble tablet was sublingually administered to each mouse. After one week from the administration, the mice were anesthetized again, and the prepared rapid soluble tablet was sublingually administered to each mouse. After one week from the second administration, a serum and a nasal cavity washing liquid of each mouse were collected, and an inactivated rabies virus-specific IgG titer in a serum and an inactivated rabies virus-specific IgA titer in a nasal cavity washing liquid were determined by the ELISA method.

TABLE 9

| No. | Vaccine antigen | | Adjuvant | | | | |
| --- | --- | --- | --- | --- | --- | --- | --- |
| | Species | Amount [/mouse/dose] | Substance name | Ligand | Amount [μg/mouse/dose] | Administration route | Note |
| Example 11 | Live attenuated rotavirus (RIX4414 strain) | Vaccine 100 uL equivalent | LPS derived from *Pantoea agglomerans* | TLR4 | 1 | Sublingual | Dry preparation |
| Example 12 | Inactivated poliovirus (type 1, type 2, type 3) | Vaccine 100 uL equivalent | LPS derived from *Pantoea agglomerans* | TLR4 | 1 | Sublingual | Dry preparation |
| Example 13 | Inactivated hepatitis A virus antigen | Vaccine 100 uL equivalent | LPS derived from *Pantoea agglomerans* | TLR4 | 1 | Sublingual | Dry preparation |
| Example 14 | Inactivated Japanese encephalitis virus | Vaccine 100 uL equivalent | LPS derived from *Pantoea agglomerans* | TLR4 | 1 | Sublingual | Dry preparation |
| Example 15 | Live attenuated mumps virus | Vaccine 100 uL equivalent | LPS derived from *Pantoea agglomerans* | TLR4 | 1 | Sublingual | Dry preparation |
| Example 16 | Live attenuated measles virus | Vaccine 100 uL equivalent | LPS derived from *Pantoea agglomerans* | TLR4 | 1 | Sublingual | Dry preparation |
| Example 17 | Live attenuated rubella virus | Vaccine 100 uL equivalent | LPS derived from *Pantoea agglomerans* | TLR4 | 1 | Sublingual | Dry preparation |
| Example 18 | Tetanus toxoid-conjugated Haemophilus influenzae type b polysaccharide | Vaccine 100 uL equivalent | LPS derived from *Pantoea agglomerans* | TLR4 | 1 | Sublingual | Dry preparation |
| Example 19 | Recombinant HBs antigen protein | Vaccine 100 uL equivalent | LPS derived from *Pantoea agglomerans* | TLR4 | 1 | Sublingual | Dry preparation |
| Example 20 | Live attenuated yellow fever virus | Vaccine 100 uL equivalent | LPS derived from *Pantoea agglomerans* | TLR4 | 1 | Sublingual | Dry preparation |
| Example 21 | Tetanus toxoid | Vaccine 100 uL equivalent | LPS derived from *Pantoea agglomerans* | TLR4 | 1 | Sublingual | Dry preparation |
| Example 22 | Live attenuated varicella-zoster virus | Vaccine 100 uL equivalent | LPS derived from *Pantoea agglomerans* | TLR4 | 1 | Sublingual | Dry preparation |
| Example 23 | Live BCG | Vaccine 30 uL equivalent | LPS derived from *Pantoea agglomerans* | TLR4 | 1 | Sublingual | Dry preparation |
| Example 24 | Inactivated rabies virus | Vaccine 200 uL equivalent | LPS derived from *Pantoea agglomerans* | TLR4 | 1 | Sublingual | Dry preparation |

Example 25

To 100 μL (1000 μg/mL) of ovalbumin (OVA) (Sigma-Aldrich Japan), and 5 μL (2 mg/mL) of a solution of a lipopolysaccharide derived from *Pantoea agglomerans* (available from Nacalai Tesque), a phosphate buffer (available from Nacalai Tesque) was added to prepare 200 μL of a mucosal vaccine composition.

Six mice (female BALE/C mice aged 8 weeks, Japan SLC, Inc.) were anesthetized, and 20 μL of the prepared vaccine composition was sublingually administered to each mouse. After one week from the administration, the mice were anesthetized again, and sublingual administration was conducted to each mouse in the same manner. After one week from the second administration, a serum and mucosal samples of each mouse were collected, and an ovalbumin-specific IgG titer in a serum, and ovalbumin-specific IgA titers in a nasal cavity washing liquid, saliva, an alveolus washing liquid, a vaginal washing liquid, and a fecal extract were determined by the ELISA method. Specific determination methods will be described later.

Comparative Example 15

To 100 μL (1000 μg/mL) of ovalbumin (OVA) (Sigma-Aldrich Japan), a phosphate buffer (available from Nacalai Tesque) was added to prepare 300 μL of a mucosal vaccine composition. The subsequent operation and evaluation are as described in Example 25.

TABLE 10

| | Vaccine antigen | | Adjuvant | | | |
|---|---|---|---|---|---|---|
| No. | Species | Amount [μg/mouse/dose] | Substance name | Ligand | Amount [μg/mouse/dose] | Administration route |
| Example 25 | Ovalbumin | 10 | LPS derived from *Pantoea agglomerans* | TLR4 | 1 | Sublingual |
| Comparative Example 15 | Ovalbumin | 10 | — | — | — | Sublingual |

Example 26

To 100 μL (1000 μg/mL) of ovalbumin (OVA) (Sigma-Aldrich Japan), and 5 μL (2 mg/mL) of a solution of a lipopolysaccharide derived from *Pantoea agglomerans* (available from Nacalai Tesque), a phosphate buffer (available from Nacalai Tesque) was added to prepare 500 μL of a mucosal vaccine composition.

Six mice (female BALB/C mice aged 8 weeks, Japan SLC, Inc.) were anesthetized, and 50 μL of the prepared vaccine composition was spray-administered to the bronchial tube of each mouse using a liquid sprayer (available from Penn-Century, Inc.). After one week from the administration, the mice were anesthetized again, and pulmonary administration was conducted to each mouse in the same manner. After one week from the second administration, a serum and mucosal samples of each mouse were collected, and an ovalbumin-specific IgG titer in a serum, and ovalbumin-specific IgA titers in a nasal cavity washing liquid, saliva, an alveolus washing liquid, a vaginal washing liquid, and a fecal extract were determined by the ELISA method. Specific determination methods will be described later.

Comparative Example 16

To 100 μL (1000 μg/mL) of ovalbumin (OVA) (Sigma-Aldrich Japan), a phosphate buffer (available from Nacalai Tesque) was added to prepare 500 μL of a mucosal vaccine composition. The subsequent operation and evaluation are as described in Example 26.

TABLE 11

| | Vaccine antigen | | Adjuvant | | | |
|---|---|---|---|---|---|---|
| No. | Species | Amount [μg/mouse/dose] | Substance name | Ligand | Amount [μg/mouse/dose] | Administration route |
| Example 26 | Ovalbumin | 10 | LPS derived from *Pantoea agglomerans* | TLR4 | 1 | Pulmonary |
| Comparative Example 16 | Ovalbumin | 10 | — | — | — | Pulmonary |

Example 27

To 100 μL (1000 μg/mL) of ovalbumin (OVA) (Sigma-Aldrich Japan), and 5 μL (2 mg/mL) of a solution of a lipopolysaccharide derived from *Pantoea agglomerans* (available from Nacalai Tesque), a phosphate buffer (available from Nacalai Tesque) was added to prepare 200 μL of a mucosal vaccine composition.

Six mice (female BALB/C mice aged 8 weeks, Japan SLC, Inc.) were anesthetized, and 20 μL of the prepared vaccine composition was administered to the vagina of each mouse with the use of a pipette. After one week from the administration, the mice were anesthetized again, and vaginal administration was conducted to each mouse in the same manner. After one week from the second administration, a serum and mucosal samples of each mouse were collected, and an ovalbumin-specific IgG titer in a serum, and ovalbumin-specific IgA titers in a vaginal washing liquid and a fecal extract were determined by the ELISA method. Specific determination methods will be described later.

Comparative Example 17

To 100 μL (1000 μg/mL) of ovalbumin (OVA) (Sigma-Aldrich Japan), a phosphate buffer (available from Nacalai Tesque) was added to prepare 200 μL of a mucosal vaccine composition. The subsequent operation and evaluation are as described in Example 27.

TABLE 12

| No. | Vaccine antigen | | Adjuvant | | | Administration route |
|---|---|---|---|---|---|---|
| | Species | Amount [μg/mouse/dose] | Substance name | Ligand | Amount [μg/mouse/dose] | |
| Example 27 | Ovalbumin | 10 | LPS derived from *Pantoea agglomerans* | TLR4 | 1 | Transvaginal |
| Comparative Example 17 | Ovalbumin | 10 | — | — | — | Transvaginal |

Example 28

To 100 μL (1000 μg/mL) of ovalbumin (OVA) (Sigma-Aldrich Japan), and 5 μL (2 mg/mL) of a solution of a lipopolysaccharide derived from *Pantoea agglomerans* (available from Nacalai Tesque), a phosphate buffer (available from Nacalai Tesque) was added to prepare 500 μL of a mucosal vaccine composition.

Six mice (female BALB/C mice aged 8 weeks, Japan SLC, Inc.) were anesthetized, and 50 μL of the prepared vaccine composition was administered to the rectum of each mouse with the use of a 1 mL syringe and a sonde for mouse (Fuchigami Kikai). After one week from the administration, the mice were anesthetized again, and rectal administration was conducted to each mouse in the same manner. After one week from the second administration, a serum and mucosal samples of each mouse were collected, and an ovalbumin-specific IgG titer in a serum, and ovalbumin-specific IgA titers in a vaginal washing liquid and a fecal extract were determined by the ELISA method. Specific determination methods will be described later.

Comparative Example 18

To 100 μL (1000 μg/mL) of ovalbumin (OVA) (Sigma-Aldrich Japan), a phosphate buffer (available from Nacalai Tesque) was added to prepare 500 μL of a mucosal vaccine composition. The subsequent operation and evaluation are as described in Example 28.

TABLE 13

| No. | Vaccine antigen | | Adjuvant | | | Administration route |
|---|---|---|---|---|---|---|
| | Species | Amount [μg/mouse/dose] | Substance name | Ligand | Amount [μg/mouse/dose] | |
| Example 28 | Ovalbumin | 10 | LPS derived from *Pantoea agglomerans* | TLR4 | 1 | Rectal |
| Comparative Example 18 | Ovalbumin | 10 | — | — | — | Rectal |

(Mouse Immunological Experiments)

For female BALB/c mice aged 8 weeks, administration was conducted twice at an interval of one week. After one week from the last administration, blood and a nasal cavity washing liquid of each mouse were collected. The blood was centrifuged at 3000 G for 10 minutes at 4° C., and 300 μL of a phosphate buffer (available from Nacalai Tesque) was added to 20 μL of the supernatant to prepare a serum sample. Mucous membrane samples were collected in the following manner. Regarding a nasal cavity washing liquid, a cut was made in a lower part of the respiratory tract of a BALB/c mouse, 200 μL of a phosphate buffer (available from Nacalai Tesque) was poured into the respiratory tract, and a sample came into the nasal cavity was collected as a nasal cavity washing liquid sample. Regarding saliva, 500 μL of 12 μg/mL carbamylcholine chloride was administered to the abdominal cavity of a mouse to promote production of saliva, and then 20 μL of saliva was collected. Regarding an alveolus washing liquid, a cut was made in a lower part of the respiratory tract of a BALB/c mouse, 500 μL of a phosphate buffer (available from Nacalai Tesque) was poured into the lung, and the phosphate buffer came into the lung was collected as an alveolus washing liquid sample. Regarding a vaginal washing liquid, 150 μL of a phosphate buffer (available from Nacalai Tesque) was poured into the vagina of a BALB/c mouse, and a sample after pipetting 10 times was collected as a vaginal washing liquid sample. Regarding a fecal extract, 100 μL of a phosphate buffer (available from Nacalai Tesque) per 10 mg of collected faces was added, and the mixture was vortexed for 10 minutes. Thereafter, centrifugation at 3000 G was conducted for 10 minutes at 4° C., and the supernatant was collected as a fecal extract sample. By measuring an immunogen-specific IgG titer in a mouse serum, the systemic immune response was evaluated. Also, by measuring an immunogen-specific IgA titer in a mouse mucous membrane sample, the mucosal immune response was evaluated. The respective evaluation methods will be described below.

The respective evaluation results are shown in FIGS. 1 to 4 and 6 to 33.

(Method for Measuring Antigen-Specific IgG Titer in Mouse Serum (ELISA Method))

In a 96-well plate for ELISA, each 100 μL of each antigen (for example, a B/Wisconsin/1/2010(B) influenza HA antigen solution in measurement of a B/Wisconsin/1/2010(B)-specific IgG antibody titer) diluted with a carbonate buffer (2.5 μg/mL) was added, and the plate was left still overnight.

Wells were washed with a preliminarily prepared TWEEN 20-containing PBS (hereinafter, referred to as a washing liquid) three times, and after adding each 200 μL of a blocking solution prepared by diluting a blocking agent (BLOCK ACE, available from DS Pharma Biomedical Co., Ltd.) in purified water into 4 g/400 mL, the plate was left still for 2 hours at room temperature. Then, wells were washed with the washing liquid three times.

Using a solution prepared by diluting a blocking agent (BLOCK ACE, available from DS Pharma Biomedical Co., Ltd.) with a phosphate buffer (available from Nacalai Tesque) into 0.4 g/100 mL (hereinafter, referred to as a reagent diluent), the aforementioned serum sample was diluted 15 times by doubling serial dilution, each 50 μL of the solutions were added, and the plate was left still for 2 hours at room temperature.

Then, the wells were washed three times with a washing liquid, and each 100 μL of an HRP-labeled anti-mouse IgG antibody (Goat-anti-mouse IgG Fc HRP, available from BETHYL) diluted 10000 times with the reagent diluent was added, and the plate was left still for 1 hour at room temperature.

Then, the wells were washed three times with a washing liquid, and each 100 μL of a TMB solution (ELISA POD TMB kit, available from Nacalai Tesque) was added. Then, each 100 μL of a 1 M sulfuric acid solution was added, and absorbance at 450 nm of the 96-well plate was measured by a micro plate reader (168-11135CAM, available from Bio-Rad). Based on the absorbance in the serial dilution, the maximum dilution fold at which the absorbance was not less than 0.1 was determined as an IgG titer in a mouse serum, and the value was determined as a value of Log 2.

(Method for Measuring Antigen-Specific IgA Titer in Mouse Mucous Membrane Sample Washing Liquid (ELISA Method))

The method is basically the same as the method for measuring antigen-specific IgG titer, and the same operations were conducted except that the measurement sample was various mucous membrane samples, and an HRP-labeled anti-mouse IgA antibody (Goat-anti-mouse IgA a HRP, available from BETHYL) was used in place of the HRP-labeled anti-mouse IgG antibody.

(Examination Regarding Safety of LPS)

Figure 5:
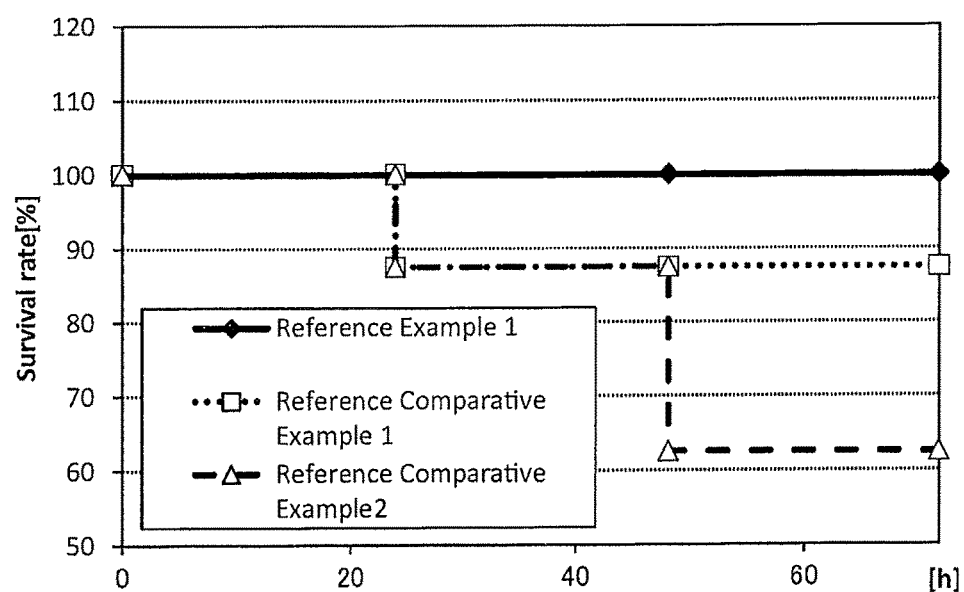
FIG. 5 is a graph showing mouse survival rates in Reference Example 1, and Reference Comparative Examples 1 and 2.
Figure 6:
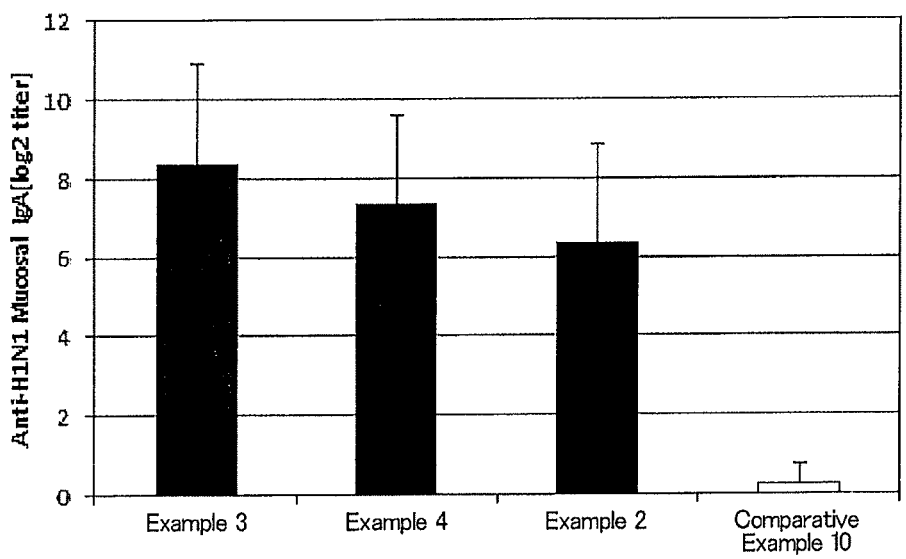
FIG. 6 is a graph showing results of influenza HA (H1N1)-specific IgA titers in a mouse nasal cavity washing liquid in Examples 2, 3, and 4, and Comparative Example 10.
Figure 7:
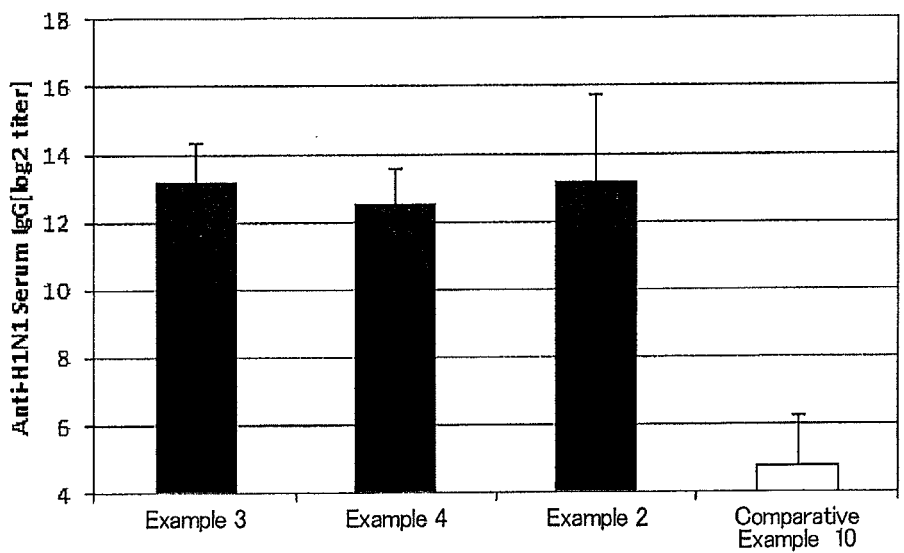
FIG. 7 is a graph showing results of influenza HA (H1N1)-specific IgG titers in a mouse serum in Examples 2, 3, and 4, and Comparative Example 10.
Figure 8:
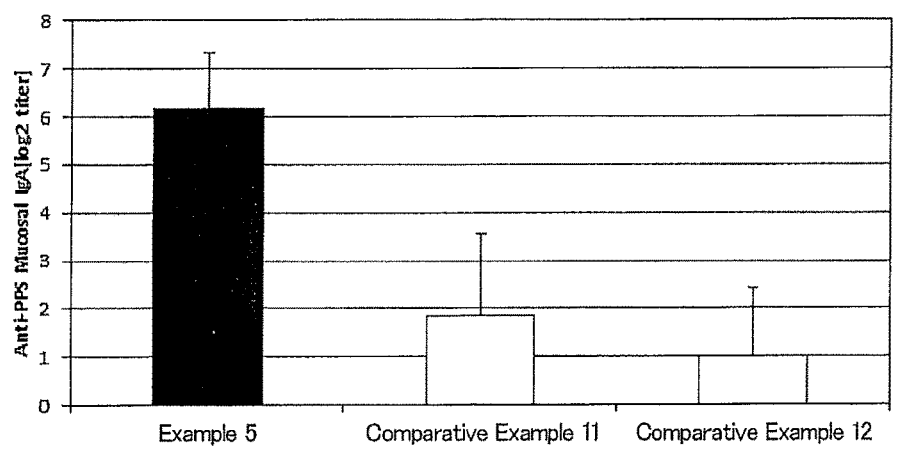
FIG. 8 is a graph showing results of pneumococcal capsular polysaccharide-specific IgA titers in a mouse nasal cavity washing liquid in Example 5, and Comparative Examples 11 and 12.
Figure 9:
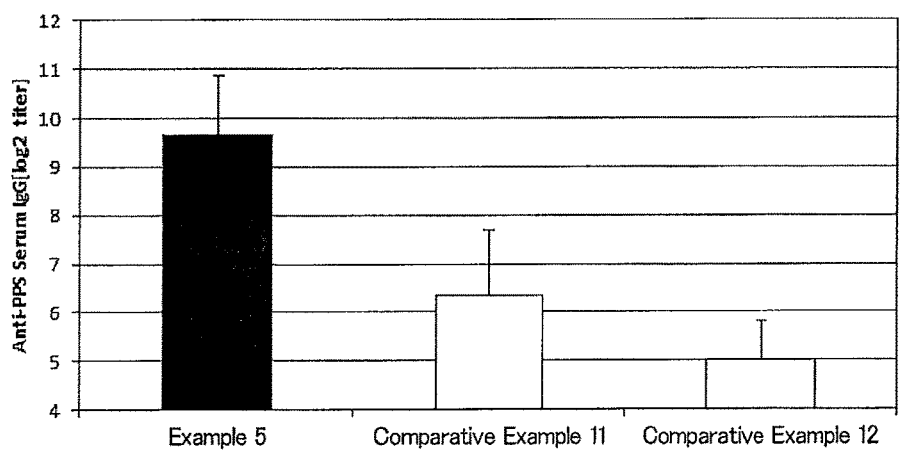
FIG. 9 is a graph showing results of pneumococcal capsular polysaccharide-specific IgG titers in a mouse serum in Example 5, and Comparative Examples 11 and 12.
Figure 10:
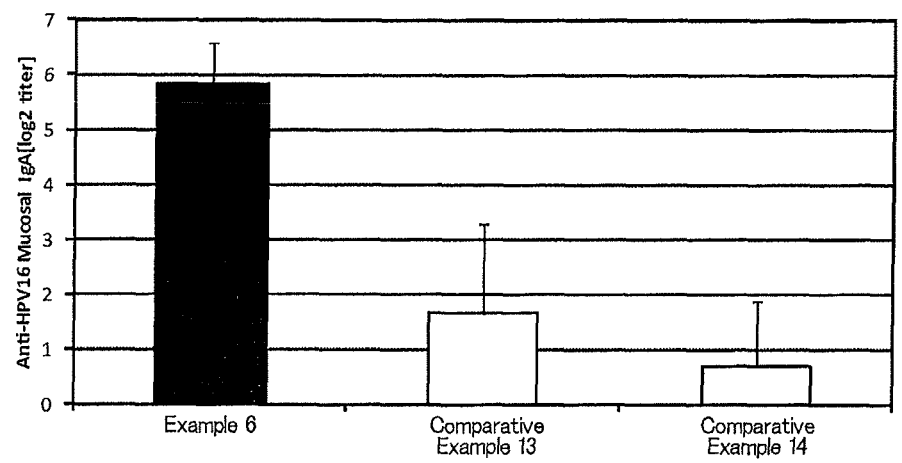
FIG. 10 is a graph showing results of HPV16-specific IgA titers in a mouse nasal cavity washing liquid in Example 6, and Comparative Examples 13 and 14.
Figure 11:
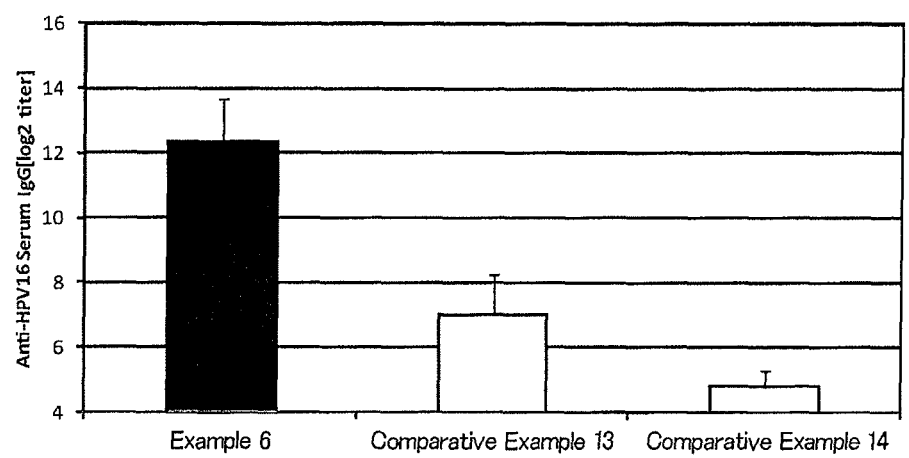
FIG. 11 is a graph showing results of HPV16-specific IgG titers in a mouse serum in Example 6, and Comparative Examples 13 and 14.
Figure 12:
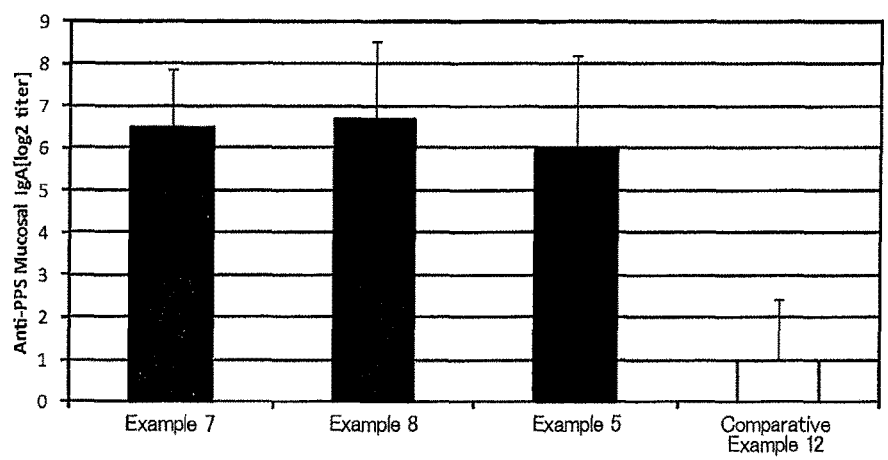
FIG. 12 is a graph showing results of pneumococcal capsular polysaccharide-specific IgA titers in a mouse nasal cavity washing liquid in Examples 5, 7, and 8, and Comparative Example 12.
Figure 13:
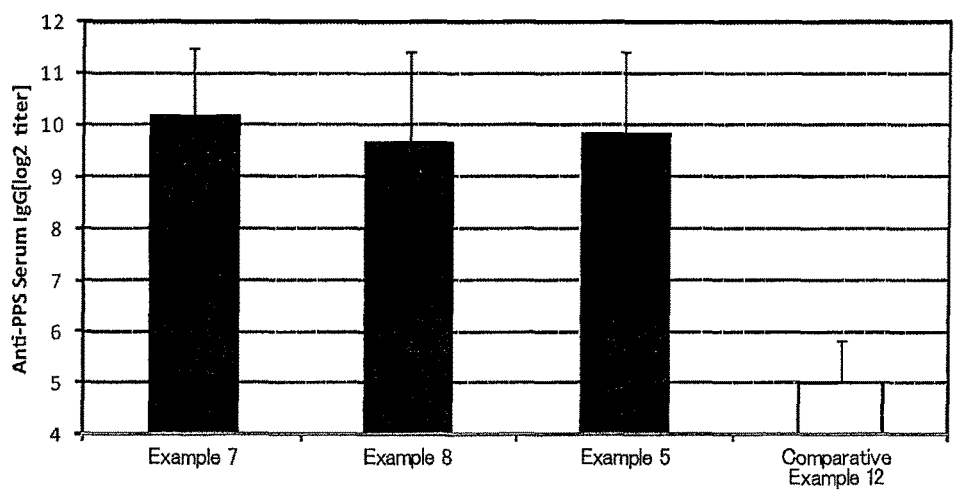
FIG. 13 is a graph showing results of pneumococcal capsular polysaccharide-specific IgG titers in a mouse serum in Examples 5, 7, and 8, and Comparative Example 12.
Figure 14:
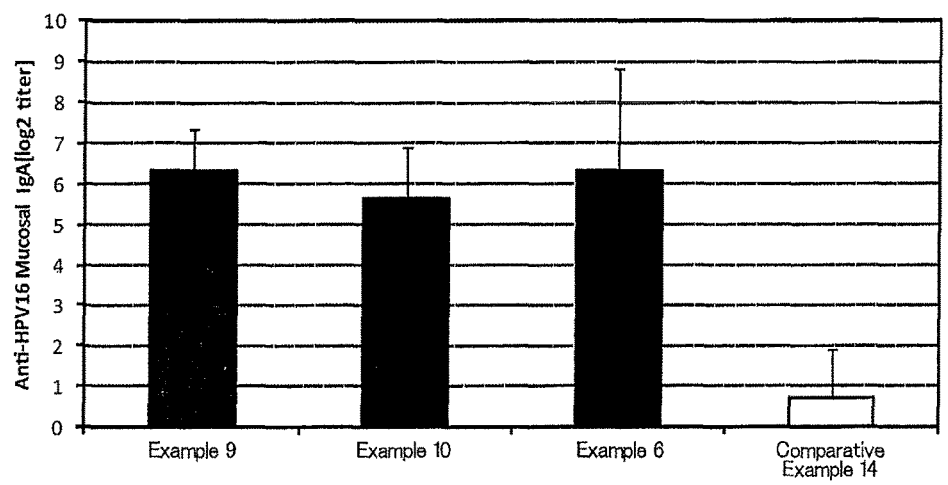
FIG. 14 is a graph showing results of HPV16-specific IgA titers in a mouse nasal cavity washing liquid in Examples 6, 9, and 10, and Comparative Example 14.
Figure 15:
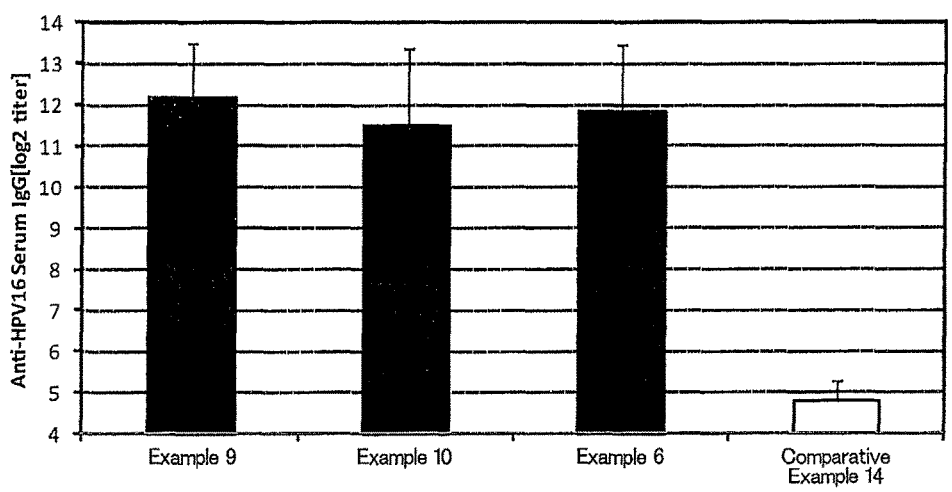
FIG. 15 is a graph showing results of HPV16-specific IgG titers in a mouse serum in Examples 6, 9, and 10, and Comparative Example 14.
Figure 16:
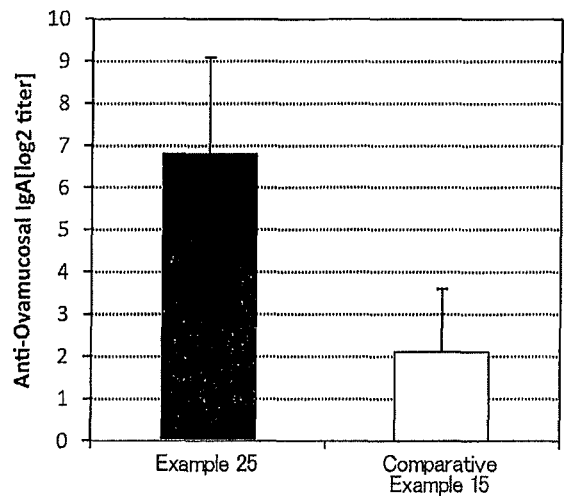
FIG. 16 is a graph showing results of OVA-specific IgA titers in a mouse nasal cavity washing liquid in Example 25 and Comparative Example 15.
Figure 17:
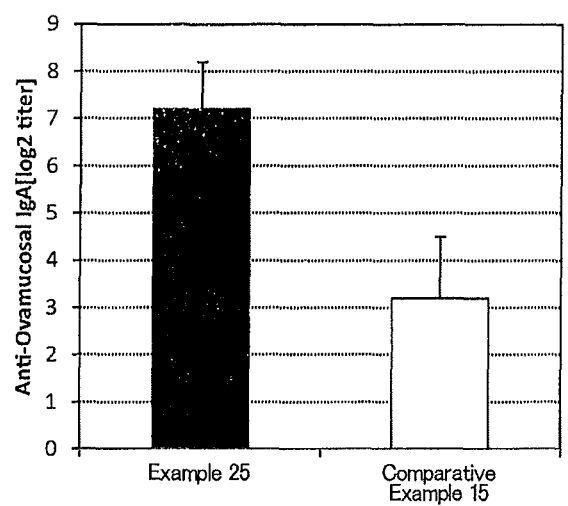
FIG. 17 is a graph showing results of OVA-specific IgA titers in a mouse saliva in Example 25 and Comparative Example 15.
Figure 18:
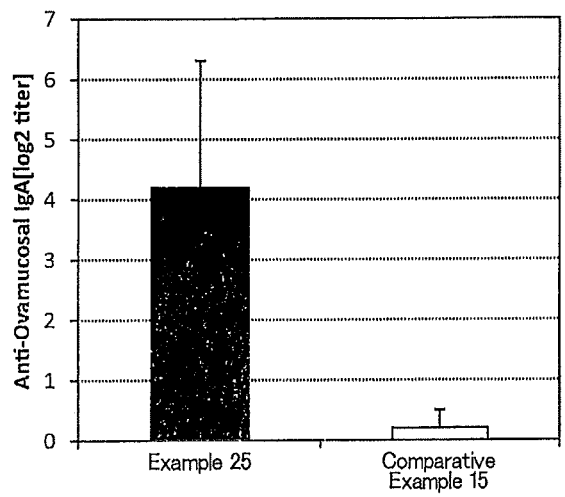
FIG. 18 is a graph showing results of OVA-specific IgA titers in a mouse alveolus washing liquid in Example 25 and Comparative Example 15.
Figure 19:
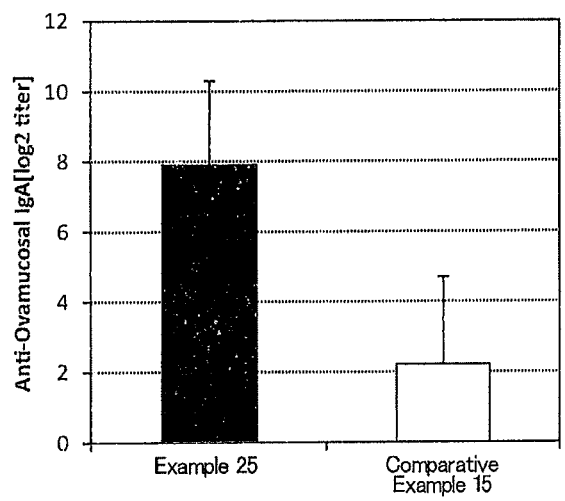
FIG. 19 is a graph showing results of OVA-specific IgA titers in a mouse vaginal washing liquid in Example 25 and Comparative Example 15.
Figure 20:
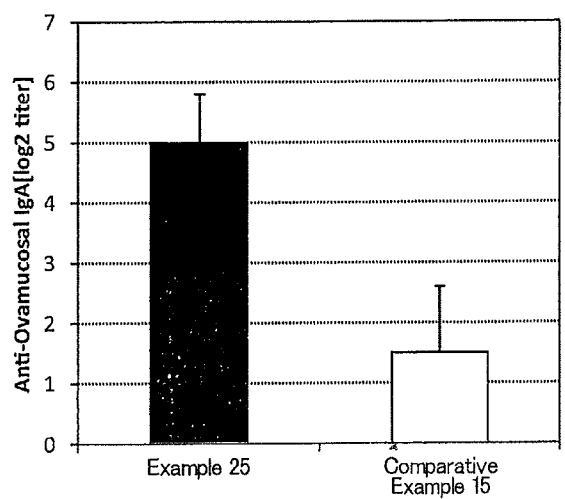
FIG. 20 is a graph showing results of OVA-specific IgA titers in a mouse fecal extract in Example 25 and Comparative Example 15.
Figure 21:
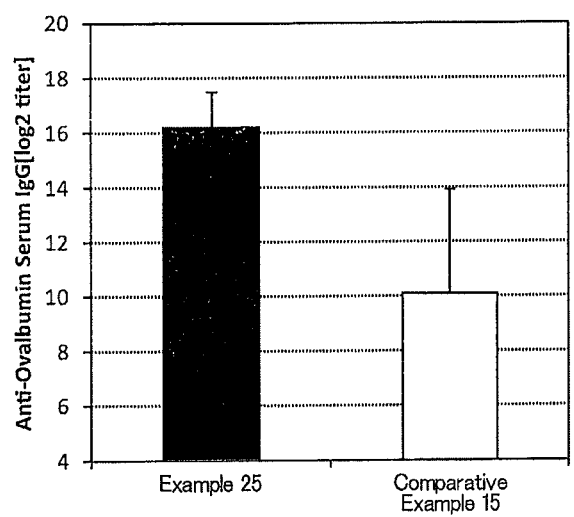
FIG. 21 is a graph showing results of OVA-specific IgG titers in a mouse serum in Example 25 and Comparative Example 15.
Figure 22:
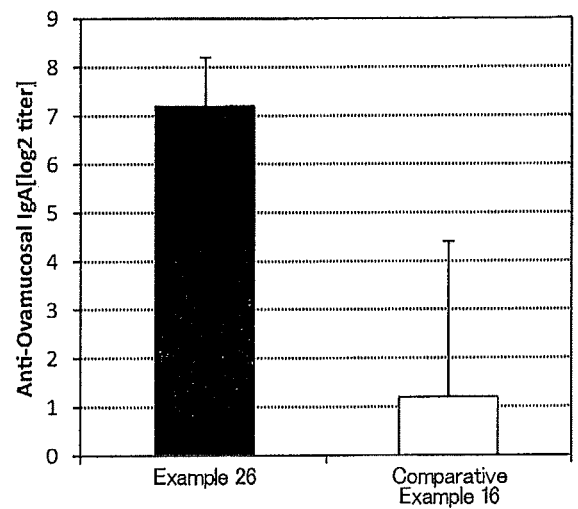
FIG. 22 is a graph showing results of OVA-specific IgA titers in a mouse nasal cavity washing liquid in Example 26 and Comparative Example 16.
Figure 23:
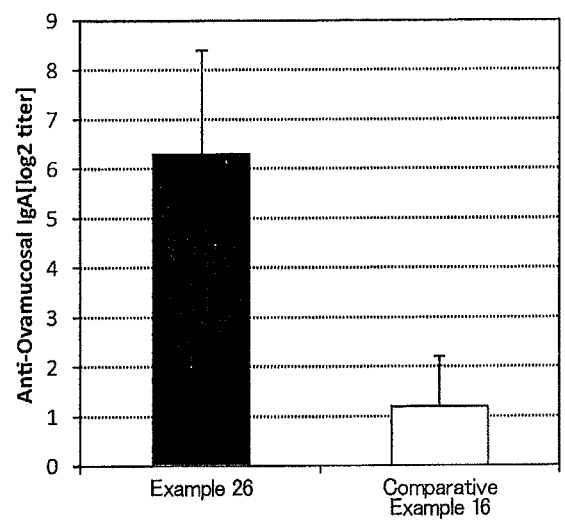
FIG. 23 is a graph showing results of OVA-specific IgA titers in a mouse saliva in Example 26 and Comparative Example 16.
Figure 24:
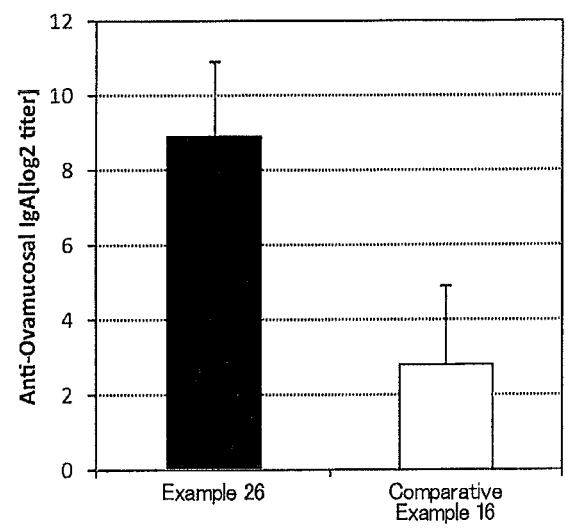
FIG. 24 is a graph showing results of OVA-specific IgA titers in a mouse alveolus washing liquid in Example 26 and Comparative Example 16.
Figure 25:
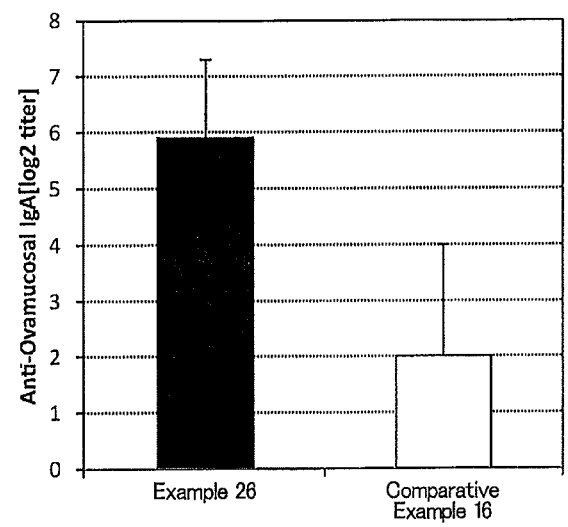
FIG. 25 is a graph showing results of OVA-specific IgA titers in a mouse vaginal washing liquid in Example 26 and Comparative Example 16.
Figure 26:
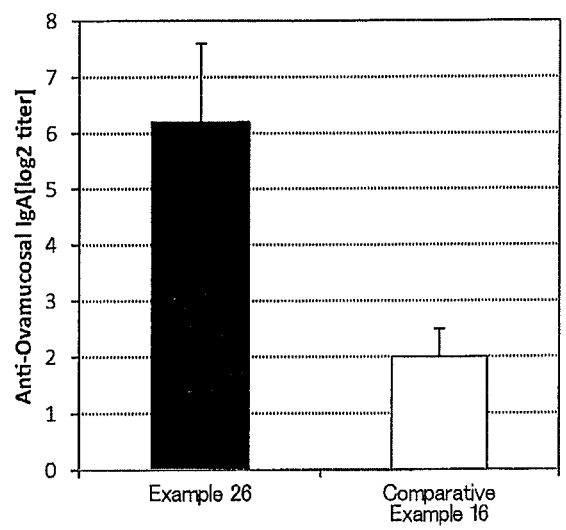
FIG. 26 is a graph showing results of OVA-specific IgA titers in a mouse fecal extract in Example 26 and Comparative Example 16.
Figure 27:
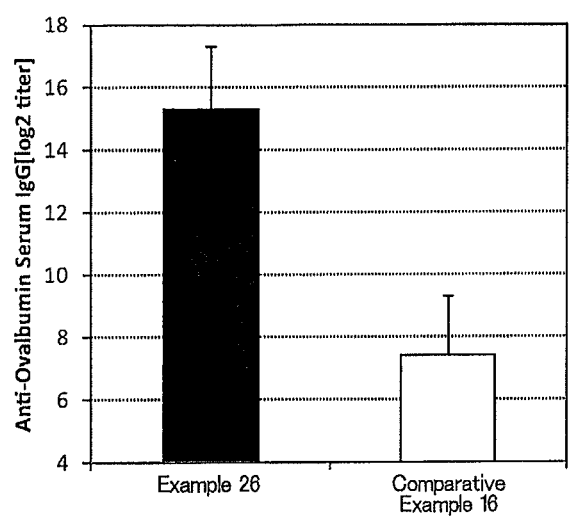
FIG. 27 is a graph showing results of OVA-specific IgG titers in a mouse serum in Example 26 and Comparative Example 16.
Figure 28:
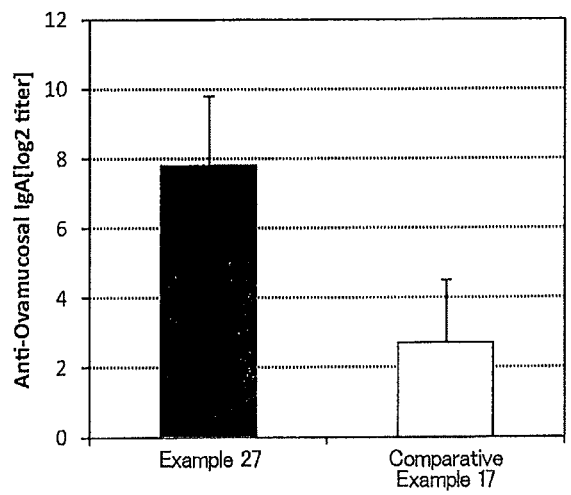
FIG. 28 is a graph showing results of OVA-specific IgA titers in a mouse vaginal washing liquid in Example 27 and Comparative Example 17.
Figure 29:
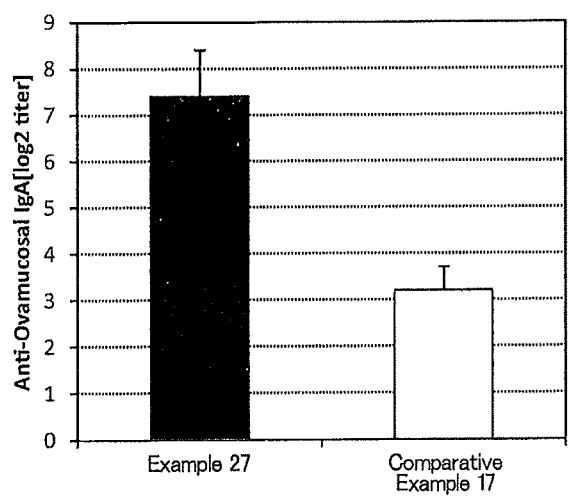
FIG. 29 is a graph showing results of OVA-specific IgA titers in a mouse fecal extract in Example 27 and Comparative Example 17.
Figure 30:
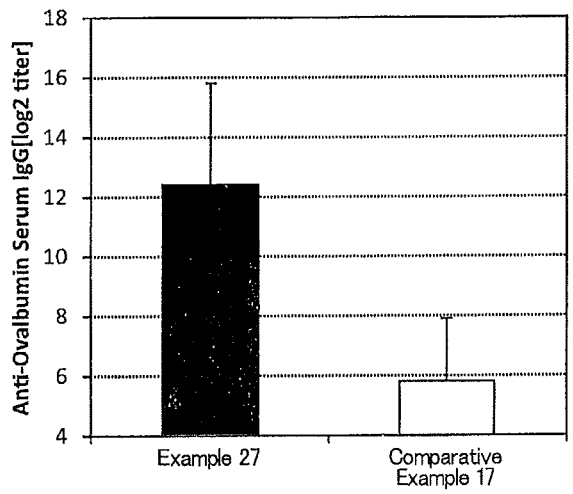
FIG. 30 is a graph showing results of OVA-specific IgG titers in a mouse serum in Example 27 and Comparative Example 17.
Figure 31:
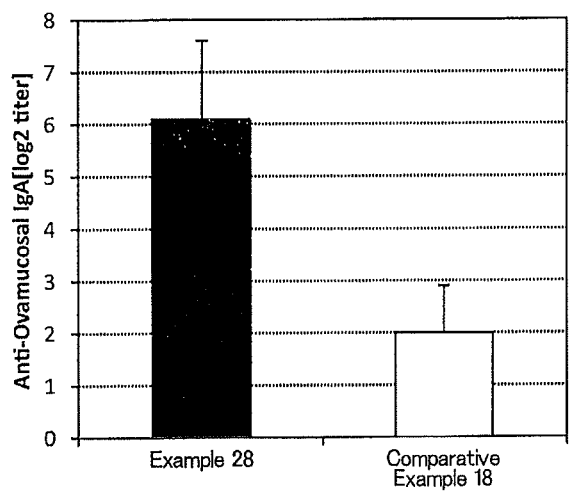
FIG. 31 is a graph showing results of OVA-specific IgA titers in a mouse vaginal washing liquid in Example 28 and Comparative Example 18.
Figure 32:
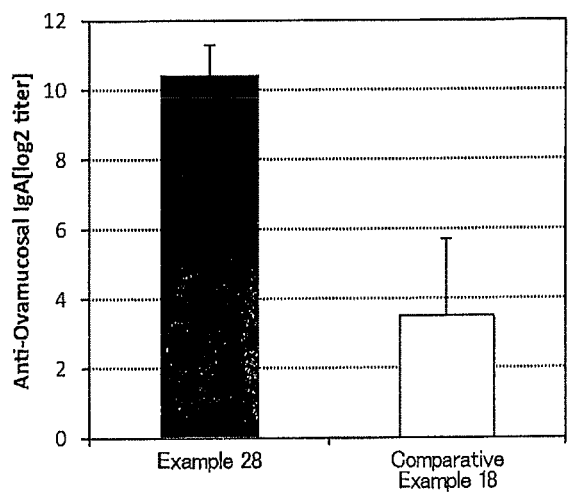
FIG. 32 is a graph showing results of OVA-specific IgA titers in a mouse fecal extract in Example 28 and Comparative Example 18.
Figure 33:
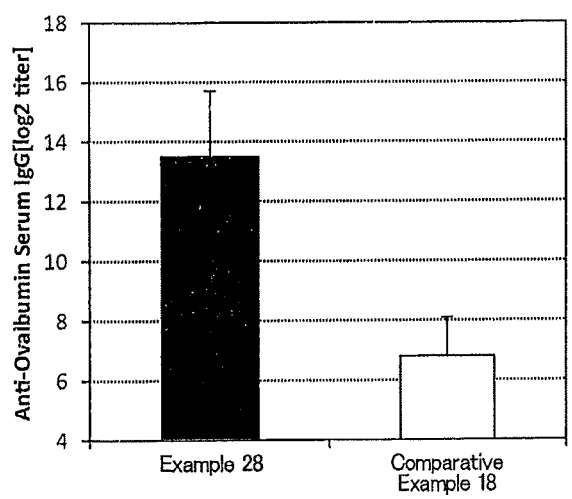
FIG. 33 is a graph showing results of OVA-specific IgG titers in a mouse serum in Example 28 and Comparative Example 18.

Each 100 μL of samples of vaccine compositions according to Reference Example 1 and Reference Comparative Examples 1 and 2 containing a type B vaccine and various LPSs was subcutaneously administered to BALB/c mice be injection. As the follow-up, the conditions of the mice were checked every 24 hours, and life or death thereof was observed. The observation was continued to 72 hours after the administration, and the survival rate was calculated. The result is shown in FIG. 5. The evaluation results are adopted as the result of safety of an LPS in mucosal vaccine compositions.

As shown in FIGS. 1 to 4 and 6 to 15, according to the examples and comparative examples, antigen-specific IgG and IgA were produced at high levels by the use of a lipopolysaccharide. On the other hand, in other comparative examples, the production amount was low with respect to the antigen-specific IgA although antigen-specific IgG was produced in some comparative examples. These results reveal that a lipopolysaccharide or a salt thereof as an adjuvant is effective for the sublingual mucosal immune induction. Also, as can be seen in FIGS. 16 to 33, it was confirmed that by administering an antigen and a lipopolysaccharide to a mucous membrane, immunity is induced not only on the mucosal surface but also on a remote mucosal surface (for example, when an antigen and a lipopolysaccharide were administered sublingually, production of antigen-specific IgA was observed on the intestinal tract and the vaginal surface). That is, it was found that a lipopolysaccharide or a salt thereof functions as an adjuvant that is effective on any mucosal surface, and is capable of sufficiently inducing antigen-specific IgA all over the body.

Also, as shown in FIG. 5, a vaccine composition containing a lipopolysaccharide derived from *Pantoea agglomerans*, a vaccine composition containing a lipopolysaccharide derived from *Escherichia coli*, and a vaccine composition containing a lipopolysaccharide derived from *Salmonella typhimurium* were compared by injection immunization, and it was confirmed that the safety of the vaccine composition containing a lipopolysaccharide derived from *Pantoea agglomerans* was high.

Therefore, considering both the immune inducing effect of mucosal administration and the safety of the administered composition, excellence of the vaccine composition containing a lipopolysaccharide derived from *Pantoea agglomerans* was confirmed.

INDUSTRIAL APPLICABILITY

Since the mucosal vaccine composition of the present invention contains the aforementioned specific adjuvant together with at least one antigen, it can induce the systemic immune response and mucosal immune response safely and effectively even when it is administered to an intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, or rectal mucous membrane.

The invention claimed is:

1. A method comprising:
   administering a mucosal vaccine composition to a mucous membrane selected from the group consisting of a human or animal intraoral mucous membrane, ocular mucous membrane, ear mucous membrane, genital mucous membrane, pharyngeal mucous membrane, respiratory tract mucous membrane, bronchial mucous membrane, pulmonary mucous membrane, gastric mucous membrane, enteric mucous membrane, and rectal mucous membrane, the mucosal vaccine composition comprising:
   at least one antigen derived from a pathogen; and
   as an adjuvant, a lipopolysaccharide derived from at least one gram-negative bacterium selected from the group consisting of *Pantoea*, *Acetobacter*, *Zymomonas*, and *Xanthomonas*, or a salt of the lipopolysaccharide;
   wherein the adjuvant does not comprise a proteosome.

2. The method according to claim 1, wherein:
   the mucosal vaccine composition is a liquid preparation, a nebular, a semisolid preparation, or a solid preparation, and
   the semi-solid preparation and the solid preparation dissolve by a body fluid and/or body temperature.

3. The method according to claim 2, wherein the mucosal vaccine composition is a solid preparation that dissolves by a body fluid and/or body temperature.

4. The method according to claim 1, wherein the method induces humoral immunity.

5. The method according to claim 2, wherein the method induces humoral immunity.

6. The method according to claim 3, wherein the method induces humoral immunity.

7. The method according to claim 1, wherein the lipopolysaccharide is derived from *Pantoea agglomerans*.

8. The method according to claim 1, wherein the solid preparation is a film preparation, a disintegrating tablet, or a soluble tablet.

9. The method according to claim 1, wherein the solid preparation is a soluble tablet.

10. The method according to claim 9, wherein the soluble tablet is a freeze-dried tablet.

* * * * *